(12) United States Patent
Astrom et al.

(10) Patent No.: US 9,993,649 B2
(45) Date of Patent: Jun. 12, 2018

(54) SYSTEM FOR PLANNING AND/OR PROVIDING A THERAPY FOR NEURAL APPLICATIONS

(71) Applicant: Medtronic Bakken Research Center B.V., Maastricht (NL)

(72) Inventors: Mattias Bengt Johan Astrom, Vasteras (NL); Johan Gerard Kleibeuker, Helvoirt (NL); Hubert Cecile François Martens, Eindhoven (NL); Gijs Antonius Franciscus Van Elswijk, Eindhoven (NL); Rutger Nijlunsing, Veldhoven (NL); Michel Marcel José Decré, Eindhoven (NL)

(73) Assignee: Medtronic Bakken Research Center B.V., Maastricht, NE (US)

(*) Notice: Subject to any disclaimer, the term of this patent is extended or adjusted under 35 U.S.C. 154(b) by 0 days. days.

(21) Appl. No.: 14/782,232

(22) PCT Filed: Mar. 28, 2014

(86) PCT No.: PCT/EP2014/056326
§ 371 (c)(1),
(2) Date: Oct. 2, 2015

(87) PCT Pub. No.: WO2014/161789
PCT Pub. Date: Oct. 9, 2014

(65) Prior Publication Data
US 2016/0045748 A1    Feb. 18, 2016

(30) Foreign Application Priority Data

Apr. 5, 2013  (EP) ..................................... 13162551
Apr. 5, 2013  (EP) ..................................... 13162588

(Continued)

(51) Int. Cl.
A61N 1/37      (2006.01)
A61N 1/372     (2006.01)
(Continued)

(52) U.S. Cl.
CPC ....... *A61N 1/37247* (2013.01); *A61N 1/0534* (2013.01); *A61N 1/36067* (2013.01); *A61N 1/36096* (2013.01); *A61N 1/36185* (2013.01)

(58) Field of Classification Search
CPC .............. A61N 1/0534; A61N 1/37247; A61N 1/36128; A61N 1/36185; A61B 5/04; A61B 5/05
See application file for complete search history.

(56) References Cited

U.S. PATENT DOCUMENTS 7,941,202 B2    5/2011  Hetke et al.
2006/0017749 A1  1/2006  McIntyre et al.
(Continued)

FOREIGN PATENT DOCUMENTS

WO    2009134475 A1    11/2009
WO    2009139917 A2    11/2009
(Continued)

OTHER PUBLICATIONS

International Preliminary Report on Patentability from International Application No. PCT/EP2014/056326, dated Oct. 6, 2015, 7 pp.
(Continued)

*Primary Examiner* — Michael Carey
*Assistant Examiner* — Natasha Patel
(74) *Attorney, Agent, or Firm* — Shumaker & Sieffert, P.A.

(57) ABSTRACT

The present invention relates to a system (10) for planning and/or providing a therapy for neural applications, especially a neurostimulation and/or neurorecording applications, comprising at least one lead (300), the lead (300)
(Continued)

Figure 1:
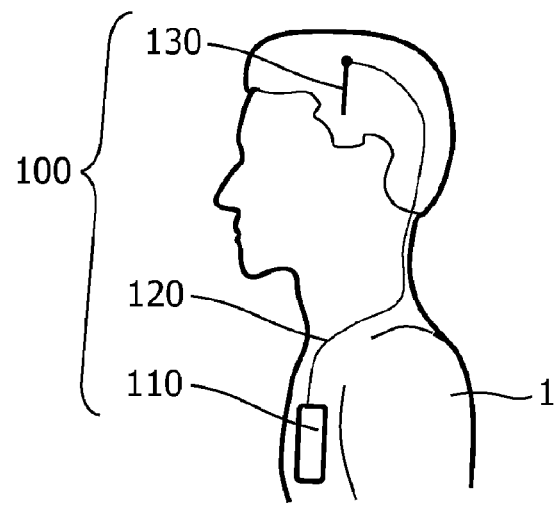

having a plurality of electrodes (132) being capable to provide at least one stimulation field (F; F1; F2), further comprising at least one adjustment means (400), the adjustment means (400) being configured such that at least one characteristic parameter of the stimulation field (F; F1; F2) is directly and/or indirectly adjusted in order to establish at least one stimulation field (F; F1; F2) with at least one user defined maximal stimulation field characteristic at at least one user defined radial distance away from the lead (300).

21 Claims, 14 Drawing Sheets

(30) Foreign Application Priority Data

| Jun. 6, 2013 | (EP) | 13170763 |
|---|---|---|
| Jun. 6, 2013 | (EP) | 13170846 |
| Jun. 6, 2013 | (EP) | 13170859 |

(51) Int. Cl.
   *A61N 1/05*   (2006.01)
   *A61N 1/36*   (2006.01)

(56) References Cited

U.S. PATENT DOCUMENTS

| 2007/0203540 A1* | 8/2007 | Goetz ............... A61N 1/0529 607/59 |
| 2009/0287271 A1 | 11/2009 | Blum et al. |
| 2011/0125214 A1 | 5/2011 | Goetz et al. |
| 2011/0191275 A1 | 8/2011 | Lujan et al. |
| 2012/0046715 A1* | 2/2012 | Moffitt ............... A61N 1/0534 607/59 |
| 2012/0165898 A1 | 6/2012 | Moffitt |
| 2012/0277821 A1* | 11/2012 | Martens ............... A61N 1/0534 607/45 |
| 2012/0302912 A1 | 11/2012 | Moffitt et al. |
| 2014/0094823 A1* | 4/2014 | Carcieri ............ A61N 1/36182 606/129 |

FOREIGN PATENT DOCUMENTS

| WO | 2010055453 A1 | 5/2010 |
| WO | 2010120823 A2 | 10/2010 |
| WO | 2011025865 A1 | 3/2011 |
| WO | 2011098937 A1 | 8/2011 |
| WO | 2012056039 A1 | 5/2012 |
| WO | 2012088482 A1 | 6/2012 |
| WO | 2012125863 A2 | 9/2012 |
| WO | 2014161789 A1 | 10/2014 |

OTHER PUBLICATIONS

International Search Report and Written Opinion of International Application No. PCT/EP2014/056326, dated Jun. 6, 2014, 4 pp.
Frankemolle et al., "Reversing cognitive-motor impairments in Parkinson's disease patients using a computational modelling approach to deep brain stimulation programming," BRAIN Journal of Neurology, Oxford University Press, Jan. 7, 2010, 746-761 pp.
Extended Search Report from counterpart European Application No. 13162588.1, dated Jul. 11, 2013, 6 pp.
Extended Search Report from counterpart European Application No. 13162551.9, dated Aug. 23, 2013, 7 pp.
Extended Search Report from counterpart European Application No. 13170859.6, dated Oct. 21, 2013, 6 pp.
Extended Search Report from counterpart European Application No. 13170763.0, dated Sep. 10, 2013, 5 pp.
Extended Search Report from counterpart European Application No. 13170846.3, dated Oct. 21, 2013, 7 pp.
Butson et al., "Current steering to control the volume of tissue activated during deep brain stimulation," National Institute of Health, Brain Stimululation, Feb. 2008, 16 pp.

* cited by examiner

SYSTEM FOR PLANNING AND/OR PROVIDING A THERAPY FOR NEURAL APPLICATIONS

This application is a national stage application under 35 U.S.C. § 371(b) of International Application No. PCT/EP2014/056326 by Astrom et al. and filed on Mar. 28, 2014, which claims the benefit of EP Application No. 13162588.1 by Astrom et al. and filed on Apr. 5, 2013, EP Application No. 13162551.9 by Astrom et al. and filed on Apr. 5, 2013, EP Application No. 13170859.6 by Astrom et al. and filed on Jun. 6, 2013, EP Application No. 13170763.0 by Astrom et al. and filed on Jun. 6, 2013, and EP Application No. 13170846.3 by Astrom et al. and filed on Jun. 6, 2013.

The present invention relates to a system for planning and/or providing a therapy for neural applications, especially a neurostimulation and/or neurorecording applications.

Implantable neurostimulation devices have been used for the past ten years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, and Tremor. New applications of DBS in the domain of psychiatric disorders (obsessive compulsive disorder, depression) are being researched and show promising results. In existing systems, the probes are connected to an implantable current pulse generator.

Currently, systems are under development with more, smaller electrodes in a technology based on thin film manufacturing. These novel systems consist of a lead made from a thin film based on thin film technology, as e.g. described in WO 2010/055453 A1. The thin film leads are fixed on a stylet material to form a probe. These probes will have multiple electrode areas and will enhance the precision to address the appropriate target in the brain and relax the specification of positioning. Meanwhile, undesired side effects due to undesired stimulation of neighbouring areas can be minimized.

Leads that are based on thin film manufacturing are e.g. described by U.S. Pat. No. 7,941,202 and have been used in research products in animal studies.

In existing systems, the DBS lead has e.g. four 1.5 mm-wide cylindrical electrodes at the distal end spaced by 0.5 mm or 1.5 mm. The diameter of the lead is 1.27 mm and the metal used for the electrodes and the interconnect wires is an alloy of platinum and iridium. The coiled interconnect wires are insulated individually by fluoropolymer coating and protected in an 80 A urethane tubing. With such electrode design, the current distribution emanates uniformly around the circumference of the electrode, which leads to stimulation of all areas surrounding the electrode.

The lack of fine spatial control over field distributions implies that stimulation easily spreads into adjacent structures inducing adverse side-effects in about 30% of the patients. To overcome this problem, systems with high density electrode arrays are being developed, hence providing the ability to steer the stimulation field to the appropriate target.

The clinical benefit of DBS is largely dependent on the spatial distribution of the stimulation field in relation to brain anatomy. To maximize therapeutic benefits while avoiding unwanted side-effects, precise control over the stimulation field is essential.

When programming neurostimulation devices the user typically define the active electrode contacts, the amplitude (current or electric potential) of one or more electrical sources that are applied to the active electrode contacts, as well as a few other electrical parameters that define the electrical pulses that are delivered to the patient. The electrical settings are then adjusted according to certain programming algorithms in order to reach an optimal therapeutic outcome.

Currently, the user has to manually and iteratively adjust the individual electrical settings in order to produce a field distribution with a specific field strength at a specific distance away from the stimulation lead.

It is therefore an object of the present invention, to improve a system for planning and/or providing a therapy for neural applications, especially a neurostimulation and/or neurorecording applications, in particular in that a field distribution of an stimulation field in connection with a therapy for neural applications with a specific field strength at a specific distance away from the stimulation lead may be set without iteratively adjust the individual electrical settings and that the adjusting may be done more intuitively.

The above object is solved according to the present invention by a system for planning and/or providing a therapy for neural applications according to claim 1. Accordingly, a system for planning and/or providing a therapy for neural applications, especially for neurostimulation and/or neurorecording applications, is provided comprising at least one lead, the lead having a plurality of electrodes being capable to provide at least one stimulation field, further comprising at least one adjustment means, the adjustment means being configured such that at least one characteristic parameter of the stimulation field is directly and/or indirectly adjusted in order to establish at least one stimulation field with at least one user defined maximal stimulation field characteristic at at least one user defined radial distance away from the lead.

By this, the advantage is achieved that a field distribution of an stimulation field in connection with a therapy for neural applications with a specific field strength at a specific distance away from the stimulation lead may be set without iteratively adjust the individual electrical settings and that the adjusting may be done more intuitively.

So, according to the invention it is now possible that during image-guided programming of neurostimulator devices, the stimulation lead and field may be visualized together with e.g. patient-specific anatomical images. With such information the advantage is achieved to let the user be in direct control of the distribution of the stimulation field, instead of the individual electrical settings.

By this invention a concept and system is provided that adjusts the stimulation amplitude in order to produce a stimulation field with a user defined maximal field strength, at a user defined radial distance away from the stimulation lead. The user defines the active electrode contacts of the lead where stimulation should be applied, as well as the desired field strength that should be distributed at a radial distance, while the system calculates and sets the electrical amplitude to produce such a field. This concept is from now on denoted as radial controlled programming.

The invention advantageously uses the fact that the distribution of the electric field and the stimulation amplitude(s) is substantially linear. When the stimulation amplitude(s) is doubled, then so is the electric field strength in the tissue. In order to perform radial controlled programming a finite element model of the stimulation lead and surrounding tissue may be used for simulations.

Especially, the lead may be a lead for neural applications, preferably a lead for a neurostimulation and/or neurorecording system. Such a neurostimulation and/or neurorecording system may be e.g. a DBS system.

The lead may e.g. comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or substantially the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

There may be an Advanced Lead Can element, which may comprise electronic means to address the plurality of electrodes and at least one Advanced Lead Can connecting means. Further, the Advanced Lead Can element may be hermetically or substantially hermetically sealed and may comprise electronic means to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 64 electrodes or more. The electrodes may be arranged such that the electrodes are substantially evenly distributed arranged all over the distal end of the lead.

Additionally, it is possible that the adjustment means is configured such that the stimulation field is automatically directly and/or indirectly adjusted. By an automatic adjustment the adjustment process is improved and can be conducted by the user more easily.

Furthermore, it is possible that the at least one stimulation field characteristic is the activation of neurons caused by the at least one stimulation field and/or the field strength of the at least one stimulation field.

It is possible that the at least one characteristic parameter of the stimulation field is the stimulation amplitude and/or stimulation energy and/or the pulse-width.

By means of the stimulation amplitude and/or stimulation energy and/or the pulse-width it is advantageously possible to influence the activation of neurons caused by the at least one stimulation field. By means of the stimulation amplitude and/or stimulation energy it is advantageously possible to influence the field strength of the at least one stimulation field.

Furthermore, it is possible that the plurality of electrodes forms a complex geometrical array and/or that the plurality of electrodes is arranged circumferentially around at least one section of the lead, especially around a section next to the distal tip end of the lead.

By means of a complex array a stimulation field of any desired shape may be formed and may be adjusted according to the patient's needs. So, a suitable and accurate tailor-made stimulation field may be provided.

A complex array may be formed by a plurality of electrodes, which are arranged circumferentially around a section next to the distal tip end of the lead. The electrodes may be e.g. arranged non-planar and non-coaxial and likewise a leopard pattern and may form a regular array. Several electrodes may form at one level a ring around the lead and the next ring may be slightly displaced such that e.g. one electrode of the second ring is partially arranged within the gap between to electrodes of the first ring. So, there are rings of electrodes in radial direction of the lead and columns of electrodes in axial direction of the lead.

Furthermore, it possible that the adjustment means comprises at least one input means for inputting the at least one characteristic parameter of the stimulation field and that the adjustment means comprises at least one visualization means which is configured such that the lead and the at least one stimulation field can be visualized, wherein the input means and the visualization means are interconnected such that a geometrical interrelation of input and visualization is provided.

By this the advantage is achieved that the at least one characteristic parameter of the stimulation field can be intuitively input by the user, since due to the geometrical interrelation of input and visualization it is clear at which location of the stimulation field an amend of the at least one characteristic parameter of the stimulation field will cause an amendment of the stimulation field.

Advantageously, by means of the interconnection input means and visualization means and the geometrical interrelation of input and visualization, the effect of the change is immediately visualized in a "what-you-see-is-what-you-get-manner" and thus creating an intuitive input possibility combined with a fast and accurate adjustment of the stimulation field.

Moreover, it is possible that the visualization means is configured such that the at least one stimulation field is displayed around an axial top view of the lead.

So, beyond the constantly updated illustration of the stimulation field the user can be enabled to interpret the status of the stimulation field immediately.

It is further possible that the input means comprises one or more input points radially arranged around the visualization of the lead.

Moreover, it is possible that the geometrical interrelation of input and visualization is provided such that the visualization of the lead and the visualization of at least one stimulation field is arranged in the center of the input means, especially in the center of the circle of input points, wherein further especially the longitudinal axis of the lead being displayed in an axial top view is in the center of the circle of input points and the stimulation field is displayed on an isosurface level which is identical to the level defined by the input points.

So, the interconnection between input means and the visualization means is displayed and provides the possibility of an instant and intuitive adjustment of the stimulation field.

Further, also a simplified illustration of the stimulation field by an axial top view of the lead can be achieved, since the dimensions of the stimulation field are directly derivable. When the input means are embodied as one or more input points radially arranged around the visualization of the lead, an intuitive input and adjustment of the stimulation field is possible for the user.

Moreover, it is possible that the adjustment means comprises at least one touch screen, wherein the touch screen is configured such that the at least one input means and the at least one visualization means are provided by the touch screen.

It is further possible that the system comprises a simulation means, wherein the simulation means is capable to calculate and/or to simulate a stimulation field for a unit amplitude(s) applied to a specific set of active electrode contacts defined by the user.

The simulation means may comprise one or more controllers and/or processing means and/or the necessary calculation means and/or storing means and/or input means and/or output means to be capable that the simulation means is configured such that the shape of the at least one stimulation field can be modelled and/or simulated such that user input is transformed into the shape of the stimulation field.

Additionally it is possible that the system is configured such that the maximum electric field strength that should be distributed at a radial distance is defined by the user, especially via the adjustment means.

Moreover, it is possible that the system 10 is configured such that the maximum electric field strength is measured at the radial distance r in the finite element simulation, wherein especially the maximum electric field strength in the finite element simulation is measured by the simulation means and wherein especially the finite element simulation is simulated and provided by the simulation means.

Furthermore, it is possible that the simulation means is capable to calculate the ratio between the measured field strength and the desired field strength.

It is also possible that the simulation means is capable to multiply the unit amplitude(s) that was used during the simulation with the ratio between the measured field strength and the desired field strength and that the result is the amplitude required to produce the desired stimulation field.

Generally, it is also possible that the system is configured and arranged as system which is connectable to a lead of system for neural applications, especially for neurostimulation and/or neurorecording applications. Accordingly, the system for planning and/or providing a therapy for neural applications, especially a neurostimulation and/or neurorecording applications, is connectable to at least one lead, the lead having a plurality of electrodes being capable to provide at least one stimulation field, further comprising at least one adjustment means, the adjustment means being configured such that at least one characteristic parameter of the stimulation field is directly and/or indirectly adjusted in order to establish at least one stimulation field with at least one user defined maximal stimulation field characteristic at at least one user defined radial distance away from the lead.

If so, the system may comprise the system features as defined above and in claims 1 to 15.

Furthermore, the following method for planning and/or providing a therapy for neural applications, especially a neurostimulation and/or neurorecording applications is disclosed.

Accordingly, the method for planning and/or providing a therapy for neural applications, especially a neurostimulation and/or neurorecording applications comprises at least the step of simulating a stimulation field for a unit amplitude(s) applied to a specific set of active electrode contacts defined by the user.

Further, it is possible that the maximum electric field strength, E, that should be distributed at a radial distance, r, is defined by the user.

Moreover, it is possible that the maximum electric field strength is measured at the radial distance r in the finite element simulation.

Additionally, it is possible that the ratio between the measured field strength and the desired field strength is calculated.

Furthermore, the unit amplitude(s) that was used during the simulation is multiplied with this ratio. The result is the amplitude required to produce the desired field.

These steps may be combined and preferably all mentioned steps of the method for planning and/or providing a therapy for neural applications, especially a neurostimulation and/or neurorecording applications are carried out in the following order:

1. A stimulation field is simulated for a unit amplitude(s) applied to a specific set of active electrode contacts defined by the user.
2. The maximum electric field strength, E, that should be distributed at a radial distance, r, are both defined by the user.
3. The maximum electric field strength is measured at the radial distance r in the finite element simulation.
4. The ratio between the measured field strength and the desired field strength is calculated.
5. The unit amplitude(s) that was used during the simulation is multiplied with this ratio. The result is the amplitude required to produce the desired field.

In order to display the desired field without having to iterate the simulation of the field using the calculated amplitude, it is possible to display the field with an isosurface level corresponding to the measured field strength in the tissue. This can be done since the size and shape of that isosurface will be identical to the desired isosurface after recalculating the field with the calculated amplitude.

Radial controlled stimulation can also be used to keep a constant but unspecified maximum field radius when the active electrode contact configuration is changed. In such case the radial distance, r, of the stimulation field is measured in the finite element simulation generated by the previous stimulation settings. This way the stimulation field radius is kept constant to the previous stimulation field settings.

Furthermore, as a part of the present disclosure also the following first alternative system for planning and/or providing a therapy for neural applications is explicitly disclosed:

During stimulation with existing DBS leads there is an option to use monopolar, bipolar, or even tripolar stimulation. Neurostimulator devices with steering brain stimulation capabilities can have a large number of electrode contacts (n>10) to which electrical settings such as current sources or grounding can be applied. Stimulation may be considered monopolar when the distance between the anode and cathode is several times larger than the distance of the cathode to the stimulation target. During monopolar stimulation in homogeneous tissue the electric field is distributed roughly spherical similar to the field from a point source. When the anode is located close to the cathode the distribution of the field becomes more directed in the anode-cathode direction. As a result the field gets denser and neurons are more likely to be activated in this area due to a higher field gradient.

The mechanisms of DBS are unknown. However, it is hypothesized that polarization (de- and/or hyperpolarization) of neural tissue is likely to play a prominent role for both suppression of clinical symptoms, as well as induction of stimulation-induced side-effects. In order to activate a neuron it has to be depolarized. Neurons are depolarized more easily close to the cathode than by the anode (about 3-7 times more depending on type of neuron, etc.).

Therefore, compared to monopolar stimulation the effect of bipolar stimulation is less spread of the electric field, a denser electric field between the anode and cathode, and more activated neurons close to the cathode. Bipolar stimulation is therefore used to focus the field to certain areas in cases when beneficial stimulation is not obtained during monopolar stimulation.

During image guided programming of the DBS device the stimulation field may be visualize to the user in various ways. Commonly, visualization techniques such as 2D contours, 3D isosurfaces, or colour-coded field maps, are used to display the distribution of the stimulation field. However, the directional component of the stimulation field, which is relevant from a neural activation point of view, is not determined and thus also not presented.

It is therefore an object of the first alternative, to improve a system for planning and/or providing a therapy for neural applications, especially a system for neurostimulation and/or neurorecording applications, and system for neural applications and a method for determining the directional component of the stimulation field, in particular in that the directional component of the stimulation field, which is relevant from a neural activation point of view, is determined and thus can be presented and visualized.

The above object is solved according to the first alternative by a system for planning and/or providing a therapy for neural applications according to aspect 1 of the first alternative system. Accordingly, a system for planning and/or providing a therapy for neural applications is provided, especially for neurostimulation and/or neurorecording applications, comprising at least one lead, the lead having a plurality of electrodes, further comprising a processing means being capable to calculate and/or to determine and/or to process characterizing data of a stimulation field being provided by the electrodes, the characterizing data of the stimulation field comprising at least two different field components, wherein the at least two different field components are a first field component having a first field vector and a second field component having a second field vector having a second field vector different from the first field vector, wherein the processing means is further configured such that the directional component of the stimulation field may be determined based on the characterizing data of the stimulation field.

By this the advantage is achieved that the directional component of the stimulation field, which is relevant from a neural activation point of view, is determined and thus can be presented and visualized.

So, a concept and system can be provided that visualizes a stimulation field, such as an electric field, dependent on the spatial direction of the stimulation field vectors, such as the electric field vectors.

The field vector may define the direction of the electric field, i.e. e.g. the stimulation field. The direction of the electric field may be defined by the force that is exerted on a positively charged particle.

Especially, the lead may be a lead for neural applications, preferably a lead for a neurostimulation and/or neurorecording system. Such a neurostimulation and/or neurorecording system may be e.g. a DBS system.

The lead may e.g. comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or substantially the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

There may be an Advanced Lead Can element, which may comprise electronic means to address the plurality of electrodes and at least one Advanced Lead Can connecting means. Further, the Advanced Lead Can element may be hermetically or substantially hermetically sealed and may comprise electronic means to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 64 electrodes or more. The electrodes may be arranged such that the electrodes are substantially evenly distributed arranged all over the distal end of the lead.

Furthermore, it is possible that the plurality of electrodes forms a complex geometrical array and/or that the plurality of electrodes is arranged circumferentially around at least one section of the lead, especially around a section next to the distal tip end of the lead.

By means of a complex array a stimulation field of any desired shape may be formed and may be adjusted according to the patient's needs. So, a suitable and accurate tailor-made stimulation field may be provided.

A complex array may be formed by a plurality of electrodes, which are arranged circumferentially around a section next to the distal tip end of the lead. The electrodes may be e.g. arranged non-planar and non-coaxial and likewise a leopard pattern and may form a regular array. Several electrodes may form at one level a ring around the lead and the next ring may be slightly displaced such that e.g. one electrode of the second ring is partially arranged within the gap between to electrodes of the first ring. So, there are rings of electrodes in radial direction of the lead and columns of electrodes in axial direction of the lead.

Furthermore it is possible that the first field component is an anodic field component and the second field component is a cathodic field component.

A cathodic field component may be provided by at least one (or more) electrode(s) through which e.g. electric current flows out. An anodic field component may be provided by at least one (or more) electrode(s) through which e.g. electric current flows in.

Additionally, it is possible that the first field component is a field component having a field vector pointing away from the lead and the second field component is a field component having a field vector pointing towards from the lead.

Moreover it is possible that the processing means is configured such that the directional component of the stimulation field is determined directly and/or indirectly by determining and/or analysing the location and the first and/or second field vector.

Furthermore, it is possible that the processing means is configured such that two components of the location and the first and/or second field vector are determined and are used for the determination of the directional component of the stimulation field, especially that only the x-component and the y-component of the location and the first and/or second field vector are determined and are used for the determination of the directional component of the stimulation field.

The vectors and also the location, which can be considered also as a vector, may comprise a x-component, a y-component and a z-component. For instance, in a case, where the longitudinal axis of the lead is located along the z-axis, only the x-component and the y-component are to be considered.

By this, the advantage is achieved that the determination process is simplified and thus accelerated. Further, the determination process requires less calculation capability of the processing means and also less storage capability of the processing means. Additionally, by this the determination problem is reduced from a 3D-problem and a 3D-calculation to a 2D-problem and a 2D-calculation.

Additionally, it is possible that the processing means is configured such that the dot product of the location and the first and/or second field vector is determined, wherein especially it is determined that the first field component is a field component having a field vector pointing away from the lead if the dot product is >0, i.e. has a value larger than zero, and the second field component is a field component having a field vector pointing towards from the lead if the dot product is <0, i.e. has a value lower than zero.

Moreover, the present invention relates to a system for neural applications with the features of aspect 8 of the first alternative. Accordingly, a system for neural applications is provided, especially a system for neurostimulation and/or neurorecording applications, for instance a deep brain stimulation system. The system for neural applications comprises at least one system for planning and/or providing a therapy for neural applications according to one of aspects 1 to 7 of the first alternative system.

Furthermore, the present invention relates to a method for determining the directional component of the stimulation field with the features of aspect 9 of the first alternative system. Accordingly, a method for determining the directional component of the stimulation field provided by the electrodes of a lead is provided, wherein the lead is a lead for neural applications, especially for neurostimulation and/or neurorecording applications, wherein characterizing data of the stimulation field comprising at least two different field components are calculated and/or determined and/or processed, wherein the at least two different field components are a first field component having a first field vector and a second field component having a second field vector having a second field vector different from the first field vector.

Additionally, it is possible that the plurality of electrodes forms a complex geometrical array and/or that the plurality of electrodes is arranged circumferentially around at least one section of the lead, especially around a section next to the distal tip end of the lead.

It is also possible that the first field component is an anodic field component and the second field component is a cathodic field component and/or the first field component is a field component having a field vector pointing away from the lead and the second field component is a field component having a field vector pointing towards from the lead.

Further, it is possible that the directional component of the stimulation field is determined directly and/or indirectly by determining and/or analysing the location and the first and/or second field vector.

Moreover, it is possible that two components of the location and the first and/or second field vector are determined and are used for the determination of the directional component of the stimulation field, especially that only the x-component and the y-component of the location and the first and/or second field vector are determined and are used for the determination of the directional component of the stimulation field.

Additionally, it is possible that the dot product of the location and the first and/or second field vector is determined, wherein especially it is determined that the first field component is a field component having a field vector pointing away from the lead if the dot product is >0, i.e. has a value larger than zero, and the second field component is a field component having a field vector pointing towards from the lead is <0, i.e. has a value lower than zero.

The method may be conducted with at least one system for planning and/or providing a therapy for neural applications according to one of aspects 1 to 7 of the first alternative system and/or a system for neural applications according to aspect 8 of the first alternative system.

It is possible that the above described method and the preferred embodiments thereto for planning and/or providing a therapy for neural applications are only used in-vitro or for testing and planning purposes only.

However, also it is also explicitly disclosed that the above described method and the preferred embodiments thereto for planning and/or providing a therapy for neural applications may be used for planning and/or providing a therapy for neural applications, especially a neurostimulation and/or neurorecording applications like DBS when the lead is implanted into the patient during therapy.

Furthermore, as a part of the present disclosure also the following second alternative system for planning and/or providing a therapy for neural applications is explicitly disclosed:

The mechanisms of DBS are unknown. However, it is hypothesized that polarization (de- and/or hyperpolarization) of neural tissue is likely to play a prominent role for both suppression of clinical symptoms, as well as induction of stimulation-induced side-effects. In order to activate a neuron it has to be depolarized. Neurons are depolarized more easily close to the cathode than by the anode (about 3-7 times more depending on type of neuron, etc.).

Therefore, compared to monopolar stimulation the effect of bipolar stimulation is less spread of the electric field, a denser electric field between the anode and cathode, and more activated neurons close to the cathode. Bipolar stimulation is therefore used to focus the field to certain areas in cases when beneficial stimulation is not obtained during monopolar stimulation.

Due to the large number of electrode contacts of neurostimulator devices that allow asymmetrical steering of the stimulation field as provided by DBS system with lead having complex electrode arrays, it is not practical to have the user manually set individual electrode contacts to ground. Also, it is not trivial to apply grounding to appropriate contacts to get a certain amount of focus. Thus, the user is currently left without support of how to ground contacts when he wishes to focus the field.

It is therefore an object of the second alternative, to improve a system for planning and/or providing a therapy for neural applications, especially a system for neurostimulation and/or neurorecording applications, in particular in that the user is supported when it is desired to focus the stimulation field provided by the electrodes of the lead and that the focusing is possible more intuitively and more accurately.

The above object is solved according to the second alternative by a system for planning and/or providing a therapy for neural applications according to aspect 1 of the second alternative system. Accordingly, a system for planning and/or providing a therapy for neural applications, especially for neurostimulation and/or neurorecording applications, comprising at least one lead, the lead having a plurality of electrodes, at least one electrode being capable to form an active contact with a first potential, wherein the system comprises at least one electrode potential adjusting means which is configured such that at least one selected electrode at (a) varying distance(s) from the active contact may be provided with a second potential different from the first potential of the active contact for the purpose of focusing the stimulation field provided by the active contact.

By this the advantage is achieved that a gradual focused stimulation field may be provided and that the user is supported when it is desired to focus the stimulation field provided by the electrodes of the lead and that the focusing is possible more intuitively and more accurately.

An active contact may be formed by one electrode. However, it is also possible that an active contact is formed by two or more electrodes. It is possible that such a plurality of electrodes consists at least partially of adjacent electrodes.

Especially, the lead may be a lead for neural applications, preferably a lead for a neurostimulation and/or neurorecording system. Such a neurostimulation and/or neurorecording system may be e.g. a DBS system.

The lead may e.g. comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or substantially the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

There may be an Advanced Lead Can element, which may comprise electronic means to address the plurality of electrodes and at least one Advanced Lead Can connecting means. Further, the Advanced Lead Can element may be hermetically or substantially hermetically sealed and may comprise electronic means to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 64 electrodes or more. The electrodes may be arranged such that the electrodes are substantially evenly distributed arranged all over the distal end of the lead.

Furthermore, it is possible that the plurality of electrodes forms a complex geometrical array and/or that the plurality of electrodes is arranged circumferentially around at least one section of the lead, especially around a section next to the distal tip end of the lead.

By means of a complex array a stimulation field of any desired shape may be formed and may be adjusted according to the patient's needs. So, a suitable and accurate tailor-made stimulation field may be provided.

A complex array may be formed by a plurality of electrodes, which are arranged circumferentially around a section next to the distal tip end of the lead. The electrodes may be e.g. arranged non-planar and non-coaxial and likewise a leopard pattern and may form a regular array. Several electrodes may form at one level a ring around the lead and the next ring may be slightly displaced such that e.g. one electrode of the second ring is partially arranged within the gap between to electrodes of the first ring. So, there are rings of electrodes in radial direction of the lead and columns of electrodes in axial direction of the lead.

Additionally, it is possible that the electrode potential adjusting means is configured such that at least one selected electrode at (a) varying distance(s) from the active contact may be provided with a second potential different from the first potential of the active contact for the purpose of focusing the stimulation field provided by the active contact automatically and/or semi-automatically.

By an automatically and/or semi-automatically adjusting the advantage is achieved that the focusing of the stimulation field can be done very easy and more intuitively. A semi-automatic providing the electrodes at varying distances from the active contact with a different potential may be realized requiring a specific user input.

In particular, it is possible that, given an initial 'monopolar' stimulation setting, a concept and system can be provided that automatically applies grounding to appropriate electrode contacts to focus the stimulation field, where the amount of applied focus is controlled by the user with a scalar value e.g. a percentage. A large amount of focus corresponds to grounding of electrode contacts located close to the active electrode contacts, whereas a small amount focus corresponds to grounding of contacts located far away from the active electrode contacts.

Further, it is possible that the system is configured such that the second potential may be provided by providing and/or setting at least one electrode which is not a part of the active contact (to) a second polarity different from the first polarity of the active contact and/or by grounding at least one electrode which is not a part of the active contact.

Especially, the electrode potential adjusting means may be configured such that the second potential may be provided by providing and/or setting at least one electrode which is not a part of the active contact (to) a second polarity different from the first polarity of the active contact and/or by grounding at least one electrode which is not a part of the active contact.

For instance, groups of electrode contacts may be assigned to one or more 'cathodal' stimulation source(s). The user is then e.g. able to configure the stimulator device to deliver 'focused' stimulation, wherein during 'focused' stimulation groups of grounded electrodes are assigned adjacent to the first group of electrodes. A grading of the effect can be achieved by increasing or decreasing the distance of grounded contacts to the cathode electrode contact groups.

It is further possible that the electrode potential adjusting means is configured such that at least one electrode at (a) varying distance(s) from the active contact may be provided with at least one second potential different from the potential of the active contact for the purpose of focusing the stimulation field provided by the active contact in a first manner and that at least one electrode at (a) varying distance(s) from the active contact may be provided with at least one third potential different from the potential of the active contact for the purpose of focusing the stimulation field provided by the active contact in a second manner.

Moreover, it is possible that the second potential different from the potential of the active contact leads higher amount of focussing by setting at least one electrode next and/or adjacent from the active contact and the electrode(s) set for the second manner and that the third potential different from the potential of the active contact leads lower amount of focussing by setting at least one electrode further away from the active contact and the electrode(s) set for the first manner.

The electrodes next and/or adjacent from the active contact may be electrodes forming a ring around the active contact. The electrodes further away from the active contact may be electrodes which are e.g. not part of the ring around the active contact.

Additionally, it is possible that the electrode potential adjusting means is configured such that the Euclidian distance between at least one of the electrodes not belonging to the active contact is calculated, wherein especially the Euclidian distance between at least one of the electrodes not belonging to the active contact is calculated by means of a distance calculation.

By this, the advantage can be achieved that a mathematically based and thus exact determination of the electrodes to be changed regarding their potential can be provided.

Furthermore, it is possible that the electrode potential adjusting means is configured such that the total surface area of all electrodes with a potential different from the potential of the active contact is related to the amount of delivered current and the number of electrodes with a potential different from the potential of the active contact is adjusted according to a predetermined safety threshold value such that the charge density safety limit is not reached when focused stimulation is turned on.

By this, the advantage is achieved that the safety of the system may be increased. In particular, by this it is possible to assure that the charge density safety limit is not reached when focused stimulation is turned on, since the total surface area of e.g. all the grounded electrodes or electrodes with a different polarity is related to the amount of delivered current and the number of grounded electrodes or electrodes with a different polarity may be then adjusted accordingly.

Moreover, it is possible that the electrode potential adjusting means is configured such that the different potential may be gradually and/or stepwise decreased and/or increased.

Moreover, the present invention relates to a system for neural applications with the features of aspect 9 of the second alternative system. Accordingly, a system for neural applications is provided, especially a system for neurostimulation and/or neurorecording applications, for instance a deep brain stimulation system. The system for neural applications comprises at least one system for planning and/or providing a therapy for neural applications according to one of aspects 1 to 8 of the second alternative system.

Furthermore, the following method for planning and/or providing a therapy for neural applications, especially a neurostimulation and/or neurorecording applications with the features of aspect 10 of the second alternative system is disclosed.

Accordingly, the method for planning and/or providing a therapy for neural applications, especially a neurostimulation and/or neurorecording applications comprises at least the step of providing electrodes at varying distances from the active contact with a second potential different from the first potential of the active contact for the purpose of focusing the stimulation field provided by the active contact.

The lead comprises a plurality of electrodes and at least one electrode may be capable to form an active contact.

Within the method it is possible that the different potential as the active contact is provided by providing and/or setting at least one electrode which is not a part of the active contact (to) a second polarity different from the first polarity of the active contact and/or by grounding at least one electrode which is not a part of the active contact.

The method may further comprise the step that at least one electrode at (a) varying distance(s) from the active contact may be provided with at least one second potential different from the potential of the active contact for the purpose of focusing the stimulation field provided by the active contact in a first manner and that at least one electrode at (a) varying distance(s) from the active contact may be provided with at least one third potential different from the potential of the active contact for the purpose of focusing the stimulation field provided by the active contact in a second manner, wherein in particular the second potential different from the potential of the active contact leads to a higher amount of focussing by setting at least one electrode next and/or adjacent from the active contact and the electrode(s) set for the second manner and that the third potential different from the potential of the active contact leads to a lower amount of focussing by setting at least one electrode further away from the active contact and the electrode(s) set for the first manner.

It is further possible that the method further comprises the step that the Euclidian distance between at least one of the electrodes not belonging to the active contact is calculated, wherein especially the Euclidian distance between at least one of the electrodes not belonging to the active contact is calculated by means of a distance calculation.

Furthermore it is possible that the method further comprises the step that the total surface area of all electrodes with a potential different from the potential of the active contact is related to the amount of delivered current and the number of electrodes with a potential different from the potential of the active contact is adjusted according to a predetermined safety threshold value such that the charge density safety limit is not reached when focused stimulation is turned on.

The method may be conducted with at least one system for planning and/or providing a therapy for neural applications according to one of aspects 1 to 8 of the second alternative system and/or a system for neural applications according to aspect 9 of the second alternative system.

It is possible that the above described method and the preferred embodiments thereto for planning and/or providing a therapy for neural applications are only used in-vitro or for testing and planning purposes only.

However, also it is also explicitly disclosed that the above described method and the preferred embodiments thereto for planning and/or providing a therapy for neural applications may be used for planning and/or providing a therapy for neural applications, especially a neurostimulation and/or neurorecording applications like DBS when the lead is implanted into the patient during therapy.

Furthermore, as a part of the present disclosure also the following third alternative system for planning and/or providing a therapy for neural applications is explicitly disclosed:

Currently, the programming procedure of neurostimulation devices is performed by defining the active electrode contacts, the amplitudes (current or electric potential) of one or more electrical sources that are applied to the active electrode contacts, as well as a few other electrical parameters that define the electrical pulses that are delivered to the patient. The patient is assessed and the electrical settings are adjusted according to certain programming algorithms in order to reach an optimal therapeutic outcome. The procedure is performed without any visual aid of the distribution of the stimulation field.

Novel DBS devices are currently being developed that allow asymmetrical steering of the stimulation field in relation to the principal axes of the stimulation lead. The ability to steer the stimulation field is from now on denoted as steering brain stimulation. Steering brain stimulation provides additional possibilities as well as complexity to the programming procedure. In order to keep the programming procedure reasonable quick and to make use of the added features there is a need for tools that support the programming procedure. One way to support the programming procedure is to visualize the distribution of the stimulation field and provide tools for the programmer to interact and control the distribution of the stimulation field.

During programming of neurostimulator devices with steering brain stimulation capabilities, the programmer may be faced with a large number of electrode contacts (n>10) to which electrical settings can be applied. When the electric field is asymmetrically steered in one (or several) directions the electrical settings of individual electrode contacts need to be adjusted. In order to keep the programming procedure reasonable time-efficient it is not feasible to manually adjust the electrical settings on an individual contact basis. Thus, there is a need for a tool with intuitive controls with which the programmer can steer the stimulation field.

Figure 10:
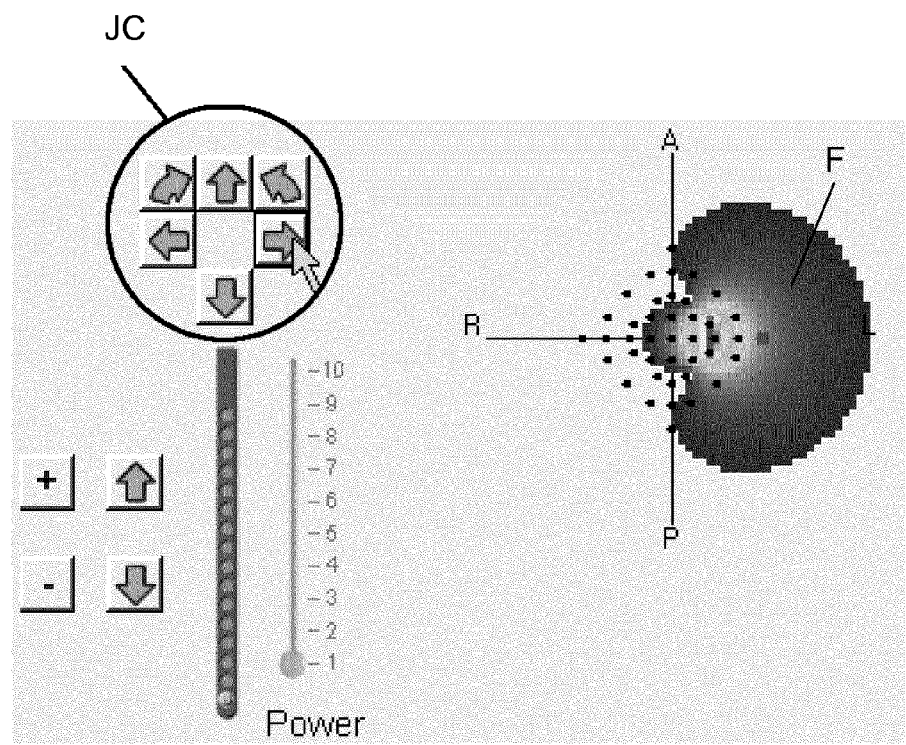
Figure 11:
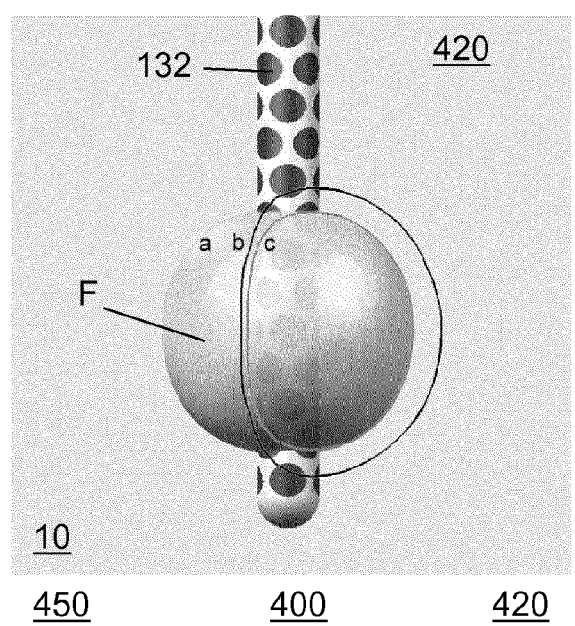
Figure 12:
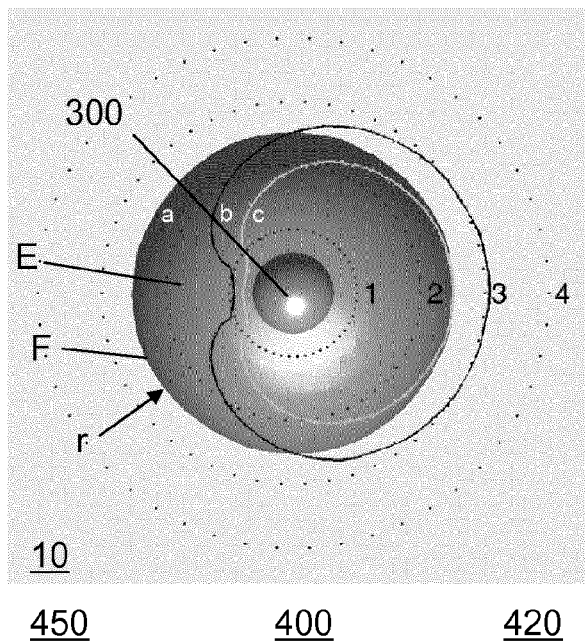

Stimulation fields from devices that provide steering functionality are commonly controlled with buttons that are organized in a joystick like manner (see e.g. FIG. 10). With a joystick control the stimulation field is moved asymmetrically around the centre of the lead. However, moving the field into a certain direction may from a clinical point of view not be the most intuitive way of controlling the field during neurostimulation. It may be hypothesised that steering is primarily going to be used when unwanted stimulation-induced side-effects are encountered. In such case it is hypothesised that the user would like to turn off or reduce intensity of certain parts of the field in the anatomical direction where the side effect is suspected to be related, rather than moving the field away from a certain direction where the field will enter new tissue in the opposite direction (FIGS. 11 and 12). Another limitation of the joystick approach is that the field can only be steered in one direction at a time. Thus, there is a need for a steering means that can provide intuitive control of the stimulation field during steering without limiting the degrees of freedom provided by the stimulation hardware device.

It is therefore an object of the third alternative to improve a system for planning and/or providing a therapy for neural applications, especially for neurostimulation and/or neurorecording applications, in particular in that a tool with intuitive controls with which the programmer can steer the stimulation field and a steering means that can provide intuitive control of the stimulation field during steering without limiting the degrees of freedom provided by the stimulation hardware device is provided.

The above object is solved with a system for planning and/or providing a therapy for neural applications with the features of aspect 1 of the third alternative system. Accordingly, a system for planning and/or providing a therapy for neural applications is provided, especially for neurostimulation and/or neurorecording applications, comprising at least one lead, the lead having a plurality of electrodes being capable to provide at least one stimulation field, further comprising at least one adjustment means being capable to adjust the stimulation field in multiple directions and at least one steering means being capable to steer the stimulation field in multiple directions simultaneously.

By this, the advantage is achieved that a tool with intuitive controls is provided with which the programmer can steer the stimulation field and a steering means that can provide intuitive control of the stimulation field during steering without limiting the degrees of freedom provided by the stimulation hardware device.

Especially, the lead may be a lead for neural applications, preferably a lead for a neurostimulation and/or neurorecording system. Such a neurostimulation and/or neurorecording system may be e.g. a DBS system.

The lead may e.g. comprise at least one thin film, whereby the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or substantially the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

There may be an Advanced Lead Can element, which may comprise electronic means to address the plurality of electrodes and at least one Advanced Lead Can connecting means. Further, the Advanced Lead Can element may be hermetically or substantially hermetically sealed and may comprise electronic means to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 64 electrodes or more. The electrodes may be arranged such that the electrodes are substantially evenly distributed arranged all over the distal end of the lead.

For instance, it is advantageously possible that the adjustment means is configured such that the shape of the at least one stimulation field can be modelled such that user input via the steering means is transformed into the shape of the stimulation field. By this, the advantage is achieved that no adjustment of the parameters of each and every electrode must be input by the user. It is possible to form the desired stimulation field directly and so the parameters of the electrodes involved to provide the required and desired shape of the stimulation field are correctly set, advantageously automatically by the system.

The adjustment means may comprise one or more controllers and/or processing means and/or the necessary calculation means and/or storing means and/or input means and/or output means to be capable that the adjustment means is configured such that the shape of the at least one stimulation field can be modelled such that user input via the steering means is translated into the shape of the stimulation field.

Furthermore, it is possible that the adjustment means is configured such that the shape of the stimulation field is transformed into stimulation settings to provide the at least one stimulation field with electrodes of the lead.

Advantageously, it is possible that the adjustment means is configured such that the stimulation field is automatically directly and/or indirectly adjusted.

Furthermore, it is possible that the plurality of electrodes forms a complex geometrical array and/or that the plurality of electrodes is arranged circumferentially around at least one section of the lead, especially around a section next to the distal tip end of the lead.

A complex array may be formed by a plurality of electrodes, which are arranged circumferentially around a section next to the distal tip end of the lead. The electrodes may be e.g. arranged non-planar and non-coaxial and likewise a leopard pattern and may form a regular array. Several electrodes may form at one level a ring around the lead and the next ring may be slightly displaced such that e.g. one electrode of the second ring is partially arranged within the gap between to electrodes of the first ring. So, there are rings of electrodes in radial/circumferential direction of the lead and columns of electrodes in axial direction of the lead.

Moreover, it is possible that the adjustment means comprises at least one the visualization means which is configured such that the lead and the at least one stimulation field can be visualized, wherein the steering means and the visualization means are interconnected such that a geometrical interrelation of input and visualization is provided.

By this the advantage is achieved that the at least one characteristic parameter of the stimulation field can be intuitively input by the user, since due to the geometrical interrelation of input and visualization it is clear at which location of the stimulation field an amend of the at least one characteristic parameter of the stimulation field will cause an amendment of the stimulation field.

Advantageously, by means of the interconnection input means and visualization means and the geometrical interrelation of input and visualization, the effect of the change is immediately visualized in a "what-you-see-is-what-you-get-manner" and thus creating an intuitive input possibility combined with a fast and accurate adjustment of the stimulation field.

It is further possible that the visualization means is configured such that the at least one stimulation field is displayed around an axial top view of the lead.

So, beyond the constantly updated visualization of the stimulation field the user shall be enabled to interpret the status of the stimulation field immediately.

Moreover, it is possible that the steering means comprises one or more first input points radially arranged around the visualization of the lead, wherein especially the first input points are capable to adjust the at least one stimulation field in radial direction.

In respect of a simplified visualization of the stimulation field by an axial top view, the input means may be embodied as one or more input points radially arranged around the visualization of the lead. So, the interconnection between input means and the visualization means is visualized and provides the possibility of an instant adjustment of the stimulation field.

It is further possible that the steering means comprises one or more second input points arranged adjacent, especially parallel, to the visualization of the lead, wherein especially the second input points are capable to adjust the at least one stimulation field in axial direction.

By this the advantage is achieved that e.g. the relevant electrodes along the axis of the lead may be switched on and/or off and may be e.g. adjusted regarding their output. In case that the arrangement is parallel it is immediately clear at which level the electrodes are activated and adjusted.

Further, it is possible that for example controls e.g. of the relevant electrodes along the axis of the lead may be provided which may result in specific configurations of stimulation settings.

Additionally, it is possible that the first input points and/or second input points of the steering means are configured such that the first input points and/or second input points can be switched between two or more states related to at least one stimulation field characteristic.

The states may be e.g. 'On', 'Off', 'Half', 'Quarter', or other values related to the stimulation amplitude or the like.

Additionally, it is possible that the at least one characteristic of the stimulation field is the stimulation amplitude and/or stimulation energy and/or the pulse-width and/or parameters which are directly and/or indirectly influencing the stimulation amplitude and/or stimulation energy and/or the pulse-width.

Moreover, it is possible that the first input points and/or second input points of the steering means are configured such that the first input points and/or second input points can be arranged in a first rotated arrangement to an unfolded visualization of at least a part of electrodes provided by the visualization means and that the first input points and/or second input points can be arranged in a second aligned arrangement to an unfolded visualization of at least a part of electrodes provided by the visualization means.

The part of electrodes may be a ring of electrodes, especially two adjacent rings of electrodes. The first rotated arrangement to an unfolded visualization of at least one part of electrodes may be a visualization setup, wherein the electrodes of the ring next to the input points are arranged such that two input points are associated to at least one electrode. The second aligned arrangement to an unfolded visualization of at least one part of electrodes may be a visualization setup, wherein the electrodes of the ring next to the input points are arranged such that one input point is associated to the electrode, the next input point is associated to a gap between two adjacent electrodes etc.

It is possible that it may be switched between the first rotated arrangement to the second aligned arrangement and vice versa.

Additionally, it is possible that the steering means is configured such that the stimulation field may be at least partially tilted and/or sloped and/or rotated.

Tilting and/or sloping and/or rotating may relate to shifting the active electrode contacts on one or more sides of the stimulation lead in the vertical direction. The effect is that the original field is tilted and/or sloped and/or rotated in one or more directions. This feature may become valuable e.g. when the user would like to tailor the stimulation field to cover the motor part of the subthalamic nucleus (STN).

Furthermore, it is possible that the geometrical interrelation of input and visualization is provided such that the visualization of the lead and the visualization of at least one stimulation field is arranged in the center of at least one part of the steering means, especially in the center of the circle of the first input points, wherein further especially the longitudinal axis of the lead being displayed in an axial top view is in the center of the circle of input points and the stimulation field is displayed on an isosurface level which is identical to the level defined by the first input points.

It is further possible that the adjustment means comprises at least one touch screen, wherein the touch screen is configured such that the at least one steering means and the at least one visualization means are provided by the touch screen.

Furthermore, the following method for planning and/or providing a therapy for neural applications, especially a neurostimulation and/or neurorecording applications is disclosed.

Accordingly, the method for planning and/or providing a therapy for neural applications, especially a neurostimulation and/or neurorecording applications comprises at least the step of simulating a stimulation field for a unit amplitude(s) applied to a specific set of active electrode contacts defined by the user.

Further, it is possible that the maximum electric field strength, E, that should be distributed at a radial distance r is defined by the user.

Moreover, it is possible that the maximum electric field strength is measured at the radial distance r in the finite element simulation.

Additionally, it is possible that the ratio between the measured field strength and the desired field strength is calculated.

Furthermore, the unit amplitude(s) that was used during the simulation is multiplied with this ratio. The result is the amplitude required to produce the desired field.

These steps may be combined and preferably all mentioned steps of the method for planning and/or providing a therapy for neural applications, especially a neurostimulation and/or neurorecording applications are carried out in the following order:
1. A stimulation field is simulated for a unit amplitude(s) applied to a specific set of active electrode contacts defined by the user.
2. The maximum electric field strength, E, that should be distributed at a radial distance, r, are both defined by the user.
3. The maximum electric field strength is measured at the radial distance r in the finite element simulation.
4. The ratio between the measured field strength and the desired field strength is calculated.
5. The unit amplitude(s) that was used during the simulation is multiplied with this ratio. The result is the amplitude required to produce the desired field.

In order to display the desired field without having to iterate the simulation of the field using the calculated amplitude, it is possible to display the field with an isosurface level corresponding to the measured field strength in the tissue. This can be done since the size and shape of that isosurface will be identical to the desired isosurface after recalculating the field with the calculated amplitude.

Radial controlled stimulation can also be used to keep a constant but unspecified maximum field radius when the active electrode contact configuration is changed. In such case the radial distance r of the stimulation field is measured in the finite element simulation generated by the previous stimulation settings. This way the stimulation field radius is kept constant to the previous stimulation field settings.

Furthermore, as a part of the present disclosure also the following fourth alternative system for planning and/or providing a therapy for neural applications is explicitly disclosed:

In existing systems, the DBS lead has e.g. four 1.5 mm-wide cylindrical electrodes at the distal end spaced by 0.5 mm or 1.5 mm. The diameter of the lead is 1.27 mm and the metal used for the electrodes and the interconnect wires is an alloy of platinum and iridium. The coiled interconnect wires are insulated individually by fluoropolymer coating and protected in an 80 A urethane tubing. With such electrode design, the current distribution emanates uniformly around the circumference of the electrode, which leads to stimulation of all areas surrounding the electrode.

The lack of fine spatial control over field distributions implies that stimulation easily spreads into adjacent structures inducing adverse side-effects in about 30% of the patients. To overcome this problem, systems with high density electrode arrays are being developed, hence providing the ability to steer the stimulation field to the appropriate target.

The clinical benefit of DBS is largely dependent on the spatial distribution of the stimulation field in relation to brain anatomy. To maximize therapeutic benefits while avoiding unwanted side-effects, precise control over the stimulation field is essential.

During stimulation with existing DBS leads there is an option to use monopolar, bipolar, or even tripolar stimulation. Neurostimulator devices with steering brain stimulation capabilities can have a large number of electrode contacts (n>10) to which electrical settings such as current sources or grounding can be applied. Stimulation may be considered monopolar when the distance between the anode and cathode is several times larger than the distance of the cathode to the stimulation target. During monopolar stimulation in homogeneous tissue the electric field is distributed roughly spherical similar to the field from a point source. When the anode is located close to the cathode the distribution of the field becomes more directed in the anode-cathode direction. As a result the field gets denser and neurons are more likely to be activated in this area due to a higher field gradient.

The mechanisms of DBS are unknown. However, it is hypothesized that polarization (de- and/or hyperpolarization) of neural tissue is likely to play a prominent role for both suppression of clinical symptoms, as well as induction of stimulation-induced side-effects. In order to activate a neuron it has to be depolarized. Neurons are depolarized more easily close to the cathode than by the anode (about 3-7 times more depending on type of neuron, etc.).

Therefore, compared to monopolar stimulation the effect of bipolar stimulation is less spread of the electric field, a denser electric field between the anode and cathode, and more activated neurons close to the cathode. Bipolar stimulation is therefore used to focus the field to certain areas in cases when beneficial stimulation is not obtained during monopolar stimulation.

DBS leads are typically implanted via a stereotactic neurosurgical procedure. The planning of a stereotactic procedure involves to the identification of the DBS target (e.g. the subthalamic nucleus) on the basis of the MR or CT images of the patient's head/brain and defining a point within the target nucleus. Eventually the stereotactic planning station (e.g. a computer system) provides the stereotactic coordinates of the target point. The stereotactic coordinates can be referenced externally and thus be used in the operating room to precisely navigate the DBS lead to the selected point in the brain.

DBS exerts its therapeutic effects through electric stimulation of a volume of tissue surrounding the active electrode(s). In existing planning stations the DBS target is represented/defined as a point. The disadvantage of defining the DBS target as a point is that it does not accurately reflect the characteristics of the therapeutic intervention.

In fact, the DBS lead may be regarded as the conduit to provide what is actually more relevant for therapy, namely the electric field delivered to a certain brain region. Taking the stimulation volume into account during target planning becomes even more important when future DBS systems will be able to produce complex non-uniform field shapes. Moreover, distribution of electric potential in brain tissue may depend on conductivity characteristics of the respective tissue.

Similar problems arise also in connection with drug delivery systems, systems for delivery of ultrasound energy like an array of transducers for delivery of ultrasound energy, light-emitting systems like an array of light-conductors, in particular e.g. waveguides.

It is therefore an object of the fourth alternative to improve a system for planning and/or providing a therapy for neural applications and a system for neural applications, in particular in that the effect of a treatment may be more predictable a-priori and that the optimal treatment setting may be identified.

The above object is solved according to the fourth alternative by a system for planning and/or providing a therapy for neural applications according to aspect 1 of the fourth alternative system. Accordingly, a system for planning and/or providing a therapy for neural applications is provided, especially for neurostimulation and/or neurorecording applications, comprising at least one therapy delivery means being capable to influence a volume of tissue of a patient, further comprising a steering and/or field shaping means which is configured such that at least the shape of the volume of tissue that shall be influenced by the at least one therapy delivery means may be modelled and the necessary settings and/or implantation conditions of therapy delivery means may be set accordingly.

By this the advantage is achieved that the effect of a treatment may be more predictable a-priori and that the optimal treatment setting may be identified. So, the system may identify a therapy delivery means that is able to generate electrical field shapes that match the shape or shapes of the volume of tissue that shall be influenced by the at least one therapy delivery means of the target volume indicated by the user. The ability to take the steering and/or field shaping capabilities of the therapy delivery means systems into account during the surgical planning will allow optimizing the therapy/side effect balance of the treatment already prior to of e.g. an implantation of the therapy delivery means.

Additionally, it is possible that the system comprises at least one processing means being capable to combine specific anatomical data and/or functional data and information about the volume of tissue of a patient that can be influenced by the at least one therapy delivery means, wherein the at least one steering and/or field shaping means is configured such that the therapy delivered by the therapy delivery means may be steered depending on at least one output of the processing means.

Moreover, it is possible that the therapy delivery means is or comprises a drug delivery system and/or a system for delivery of ultrasound energy like an array of transducers for delivery of ultrasound energy and/or a light-emitting system like an array of light-conductors, in particular e.g. waveguides.

For instance, the therapy delivery means is or comprises a lead for neural applications, especially for neurostimulation and/or neurorecording applications.

The lead may comprise a plurality of electrodes, wherein the lead is capable to provide and/or generate at least one stimulation field.

Especially, the lead may be a lead for neural applications, preferably a lead for a neurostimulation and/or neurorecording system. Such a neurostimulation and/or neurorecording system may be e.g. a DBS system.

The lead may e.g. comprise at least one thin film, wherein the thin film comprises a proximal end and a distal end, the lead further comprising a plurality of electrodes on the distal end of the thin film.

The thin film may include at least one electrically conductive layer, preferably made of a biocompatible material. The thin film may be assembled to the carrier and further processed to constitute the lead element. The thin film for a lead is preferably formed by a thin film product having a distal end, a cable with metal tracks and a proximal end. The distal end of the thin film may be forming a part of the distal end of the lead or substantially the distal end of the lead.

The distal end of the lead may be the end of the lead, which is in the implanted state of the lead the remote end of the lead with regard to the body surface area. In particular, in case of a lead for brain application, the distal end of the lead is the lower end of the lead, which is remote to the burr-hole of the skull, through which the lead is implanted.

There may be an Advanced Lead Can element, which may comprise electronic means to address the plurality of electrodes and at least one Advanced Lead Can connecting means. Further, the Advanced Lead Can element may be hermetically or substantially hermetically sealed and may comprise electronic means to address the plurality of electrodes on the distal end of the thin film, which is arranged at the distal end and next to the distal tip of the lead. The plurality of electrodes may comprise more than 5-10 electrodes, e.g. 16 or 32 electrodes or in preferred embodiments e.g. 40 electrodes or more. The electrodes may be arranged such that the electrodes are substantially evenly distributed arranged all over the distal end of the lead.

Furthermore, it is possible that the plurality of electrodes forms a complex geometrical array and/or that the plurality of electrodes is arranged circumferentially around at least one section of the lead, especially around a section next to the distal tip end of the lead.

By means of a complex array a stimulation field of any desired shape may be formed and may be adjusted according to the patient's needs. So, a suitable and accurate tailor-made stimulation field may be provided.

A complex array may be formed by a plurality of electrodes, which are arranged circumferentially around a section next to the distal tip end of the lead. The electrodes may be e.g. arranged non-planar and non-coaxial and likewise a leopard pattern and may form a regular array. Several electrodes may form at one level a ring around the lead and the next ring may be slightly displaced such that e.g. one electrode of the second ring is partially arranged within the gap between to electrodes of the first ring. So, there are rings of electrodes in radial direction of the lead and columns of electrodes in axial direction of the lead.

Furthermore, it is possible that the system comprises a visualization means, wherein the visualization means is capable to visualize volume of tissue of a patient to be addressed by the therapy delivery means, especially in the context of the pre-operative and/or peri-operative images of the patient.

The visualization means may be or may comprise e.g. display. Advantageously, the visualization means may be or may comprise e.g. a touch screen.

So, one advantage of this system is that the physician will be supported to predict the effect of stimulation a-priori more precisely and based thereupon may select an optimal DBS lead for the given patient, or the system may identify a DBS lead that is able to generate electrical field shapes that match the shape of the target volume indicated by the physician or any other user. The ability to take steering capabilities of DBS systems into account during the surgical planning will allow optimizing the therapy/side effect balance of DBS already prior to of lead implantation.

Additionally, it is possible that the visualization means comprises input means and output means and is configured such that patient images may be loaded and/or displayed by means of the output means and that by means of the input means a target volume of tissue of a patient may be indicated, especially via voxel painting and/or by free-form drawing of 3D volumes on the patient images.

In case that the visualization means is a touch screen the touch screen provides both the input means and the output means.

Patient images may be e.g. X-Ray images, computer tomography (CT) images or magneto resonance images (MRI) or the like and the visualization means may comprise e.g. a loading module or at least one connection which is capable to load and/or unload patient images, in particular patient images of interest like in the field of DBS patient images of the brain.

The system may comprise an identifying means which is configured such that from the indicated target volume of tissue of a patient the most optimal settings and/or implantation conditions of therapy delivery means may be identified and especially set accordingly by the steering means.

In particular, it is possible that patient images are loaded and user can indicate a target volume, e.g. by voxel painting or by free-form drawing of 3D volumes on the patient images. The software identifies from the indicated target volume (TV), i.e. the volume of tissue that shall be influenced by the at least one therapy delivery means and/or a most optimal lead that generates field-shapes overlapping with the user indicated TV. The selected lead is positioned automatically by the system in an orientation that matches the TV, or it can be placed manually by the user on the images and TV.

Further, it is possible that the visualization means is configured such that at least one or more effective shape of the volume of tissue may be displayed and that the system comprises a simulation means which is capable to provide a feed-forward simulation of the shape of the volume of tissue that shall be provided by the at least one therapy delivery means and that visualization means is configured such that patient images may be combined with a feed-forward simulation of the shape of the volume of tissue that shall be provided by the at least one therapy delivery means.

For instance, in the field of DBS, patient images (e.g. MRI/CT) may be combined with feed-forward simulation of electrical field(s) that can be produced by the to-be-implanted DBS system. The user may select a DBS lead, and for this lead several "effective" volumes can be displayed (non-polarized electric field, directionally dependent electric field, neuronal activation). Volumes can be displayed in 2D by colour coding of MRI voxels (e.g. spread of electric field indicated by red voxels), or using 3D meshes. The user can position the lead and its effective volumes in such a way that leads to an optimal result, i.e. good overlap with the TV.

Furthermore, it is possible that the simulation means is configured such that information about tissue anisotropy and/or tissue inhomogenity is used for the simulation when providing a feed-forward simulation of the shape of the volume of tissue that shall be provided by the at least one therapy delivery means.

By this, the advantage is achieved that the provided feed-forward simulation of the shape of the volume of tissue that shall be provided by the at least one therapy delivery means is more accurate. For instance, information about tissue anisotropy/inhomogeneity (deduced from e.g. MRI/diffusion tensor imaging (DTI)) may be taken into account in the simulation of the electric field model.

Moreover, it is possible that the visualization means is configured such that the user may identify a target area and may outline a desired shape of the volume of tissue (TV) that shall be influenced by the at least one therapy delivery means, wherein especially the desired shape of the volume of tissue (TV) that shall be influenced by the at least one therapy delivery means is a desired electrical field coverage volume.

For instance, the user may identify a target area and may outline desired electrical field coverage volume. The system may compute and identify the optimal lead for this and may then show the lead and stimulation capabilities on top of this.

Furthermore, it is possible that the steering and/or field shaping means is configured such that at least one boundary-condition may be input, wherein especially the boundary-condition may be input via the input means.

Additionally, it is possible that the boundary condition is a certain range of lead-implantation angles and/or a lead position relative to the target volume (e.g. lateral to the and/or a certain area to remain unaffected by stimulation).

For instance, it is possible to allow the user to provide more boundary-conditions, e.g. by demanding a certain range of lead-implantation angles, by demanding a lead position relative to the target volume (TV) (e.g. lateral to the TV), by demanding certain areas to remain unaffected by stimulation, etc. Essentially, that will narrow the search-space for lead types and may narrow the orientation/location of the lead with respect to the target volume.

Moreover, it is possible that the steering and/or field shaping means is configured such that at least the shape of the volume of tissue that shall be influenced by the at least one therapy delivery means may be modelled and the necessary settings and/or implantation conditions of therapy delivery means may be set accordingly semi-automatically and/or automatically.

By an automatically and/or semi-automatically setting the advantage is achieved that the setting of the necessary settings and/or implantation conditions of therapy delivery means can be done very easy and more intuitively. A semi-automatic setting may be realized requiring a specific user input.

Moreover, the fourth alternative relates to a system for neural applications with the features of aspect 15 of the fourth alternative system. Accordingly, a system for neural applications is provided, especially a system for neurostimulation and/or neurorecording applications, for instance a deep brain stimulation system. The system for neural applications comprises at least one system for planning and/or providing a therapy for neural applications according to one of aspects 1 to 14 of the fourth alternative system.

Furthermore, the following method for planning and/or providing a therapy for neural applications, especially a neurostimulation and/or neurorecording applications with the following features is explicitly disclosed:

Accordingly, the method for planning and/or providing a therapy for neural applications, especially a neurostimulation and/or neurorecording applications comprises at least the step of modeling at least the shape of the volume of tissue that shall be influenced by the at least one therapy delivery means and setting the necessary settings and/or implantation conditions of therapy delivery means accordingly.

Further, specific anatomical data and/or functional data and information about the volume of tissue of a patient that can be influenced by the at least one therapy delivery means may be combined and the therapy delivered by the therapy delivery means may be steered accordingly, in particular based on this combination.

A further step of the method may be the step of visualizing the volume of tissue of a patient to be addressed by the therapy delivery means, especially in the context of the pre-operative and/or pen-operative images of the patient.

Patient images may be loaded and/or displayed a target volume of tissue of a patient may be indicated, especially via voxel painting and/or by free-form drawing of 3D volumes on the patient images.

Further, from the indicated target volume of tissue of a patient the most optimal settings and/or implantation conditions of therapy delivery means may be identified and especially set accordingly by the steering means.

At least one or more effective shape of the volume of tissue (TV) may be displayed and provide a feed-forward simulation of the shape of the volume of tissue (TV) may be provided that shall be provided by the at least one therapy delivery means and patient images may be combined with a feed-forward simulation of the shape of the volume of tissue (TV) that shall be provided by the at least one therapy delivery means.

Information about tissue anisotropy and/or tissue inhomogenity may be used for the simulation when providing a feed-forward simulation of the shape of the volume of tissue (TV) that shall be provided by the at least one therapy delivery means.

Further, the user may identify a target area and may outline a desired shape of the volume of tissue that shall be influenced by the at least one therapy delivery means, wherein especially the desired shape of the volume of tissue that shall be influenced by the at least one therapy delivery means is a desired electrical field coverage volume.

Additionally, at least one boundary-condition may be input and the boundary condition can be a certain range of lead-implantation angles and/or a lead position relative to the target volume (TV) (e.g. lateral to the TV) and/or a certain area to remain unaffected by stimulation.

All steps of the method may be conducted semi-automatically and/or automatically.

It is possible that the above described method and the preferred embodiments thereto for planning and/or providing a therapy for neural applications are only used in-vitro or in-silicio (computer implementation, e.g. testing on a computer only) or for testing and planning purposes only.

However, also it is also explicitly disclosed that the above described method and the preferred embodiments thereto for planning and/or providing a therapy for neural applications may be used for planning and/or providing a therapy for neural applications, especially a neurostimulation and/or neurorecording applications like DBS when the lead is implanted into the patient during therapy.

Figure 2:
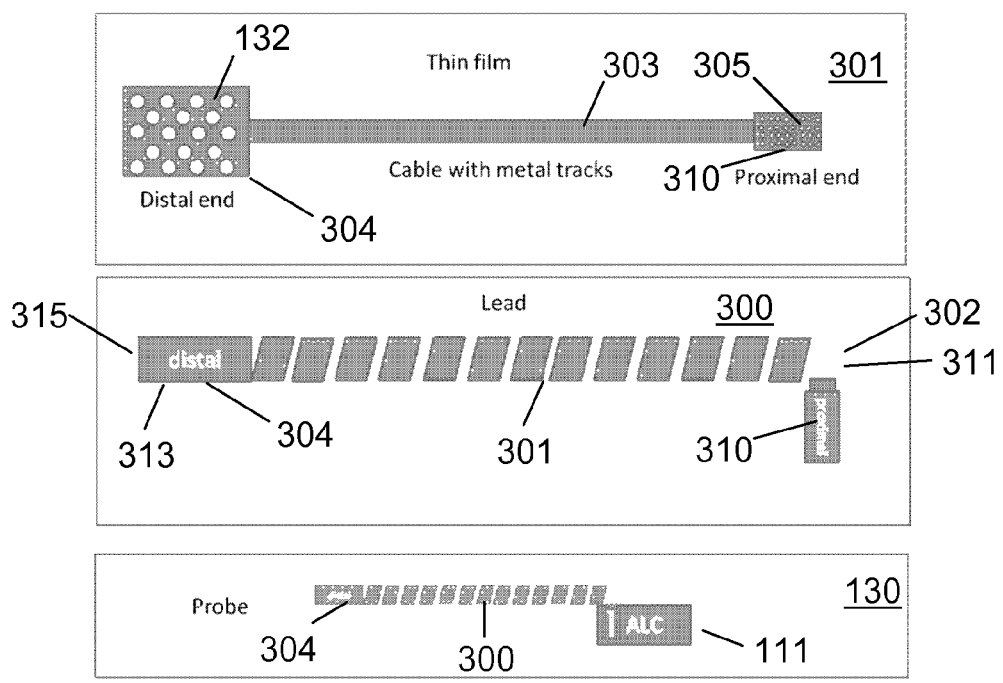
Figure 3:
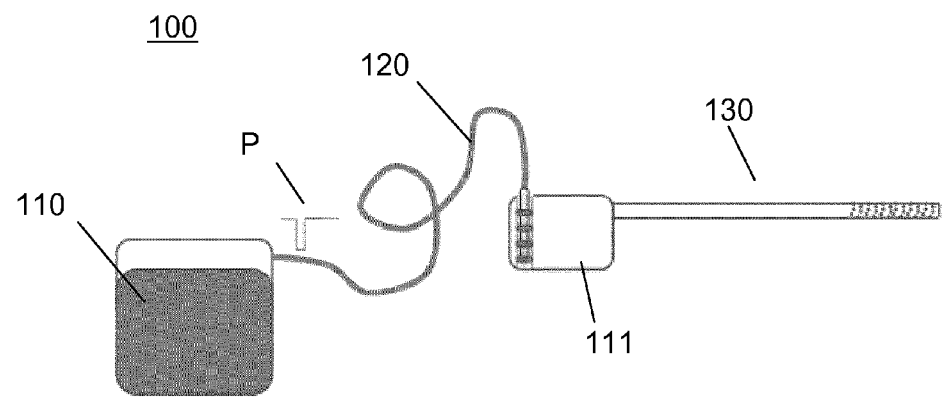
Figure 4:
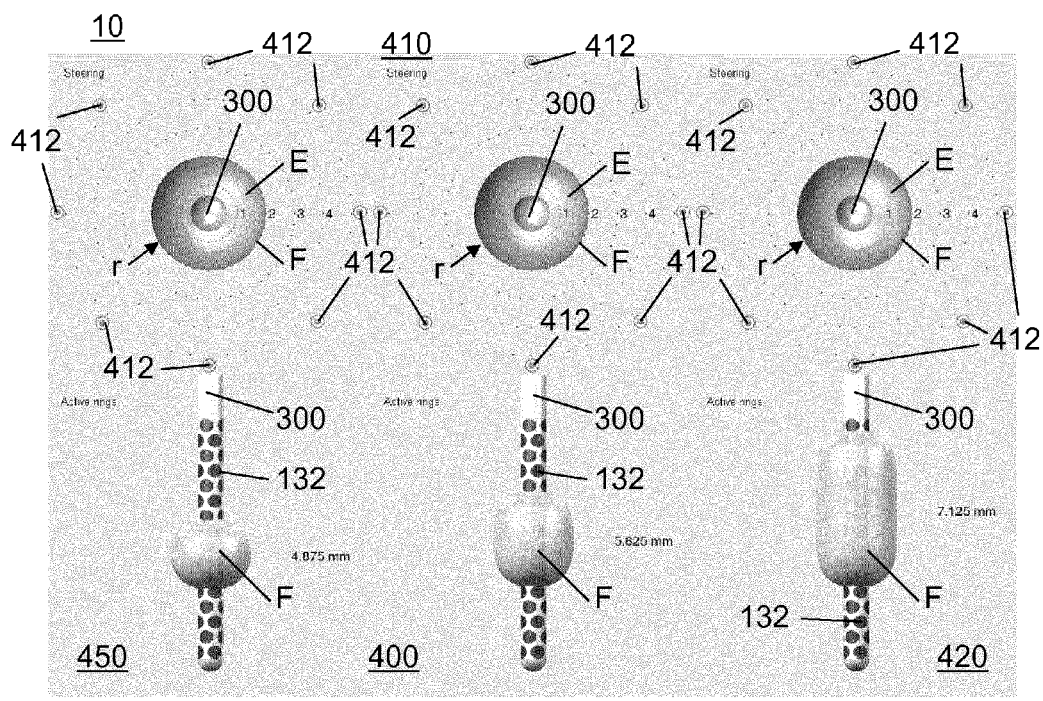
Figure 5:
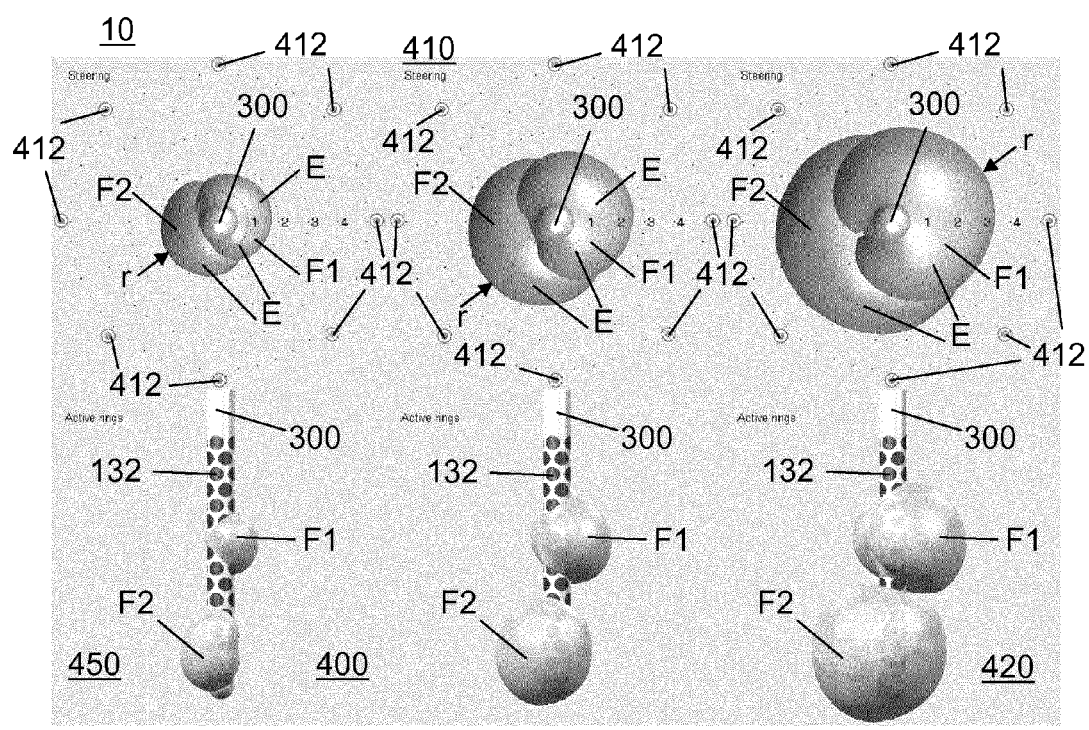
Figure 6:
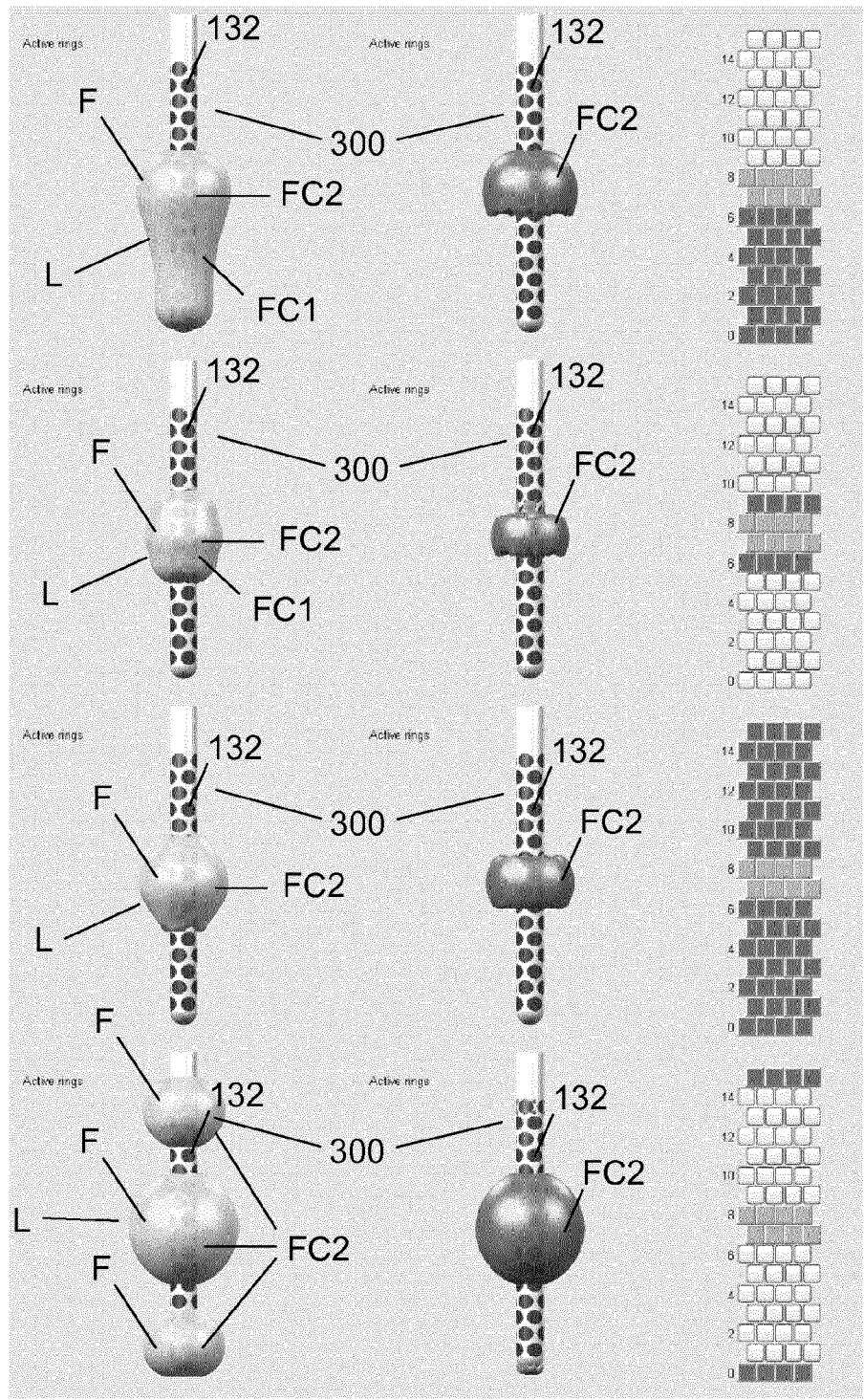
Figure 9:
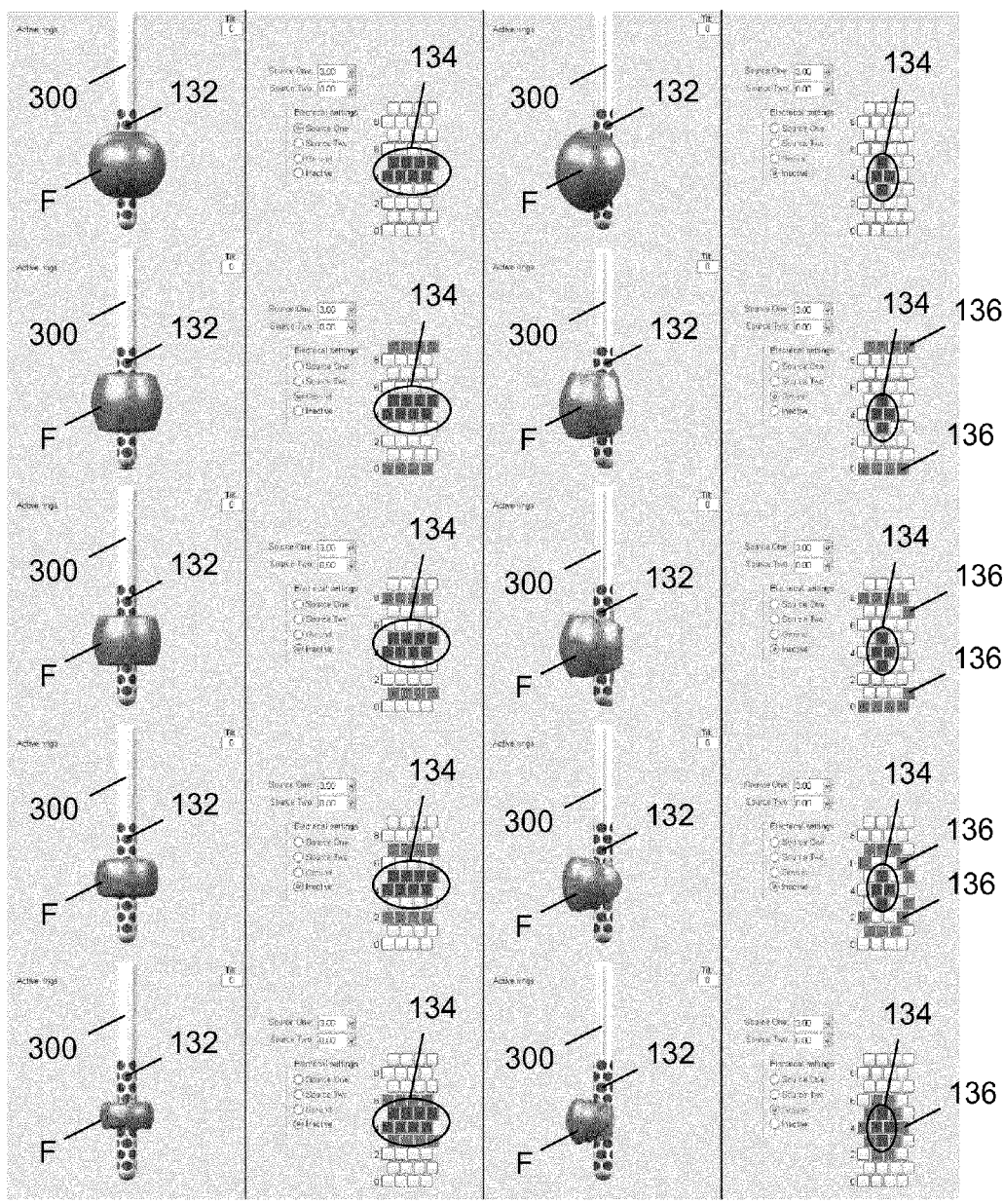
Figure 13:
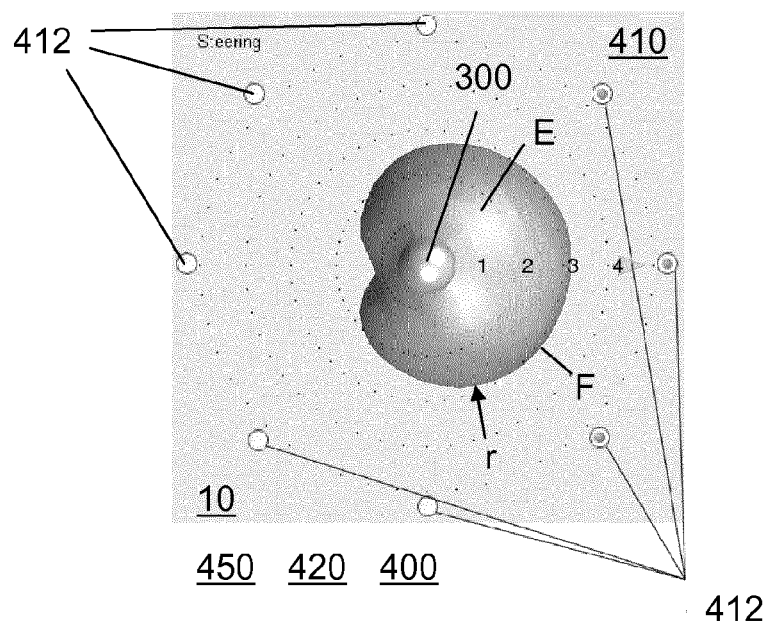
Figure 14:
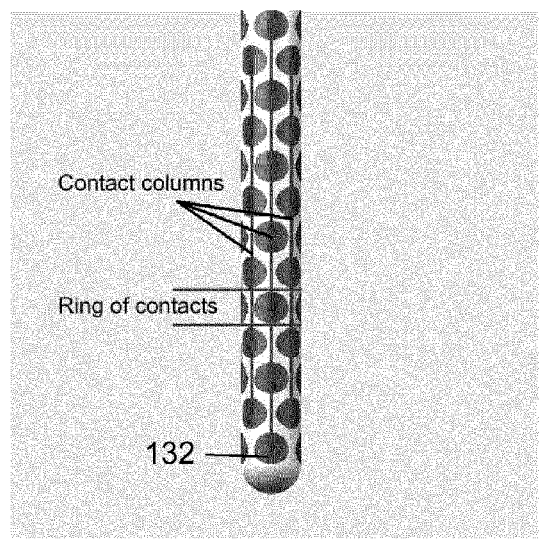
Figure 15:
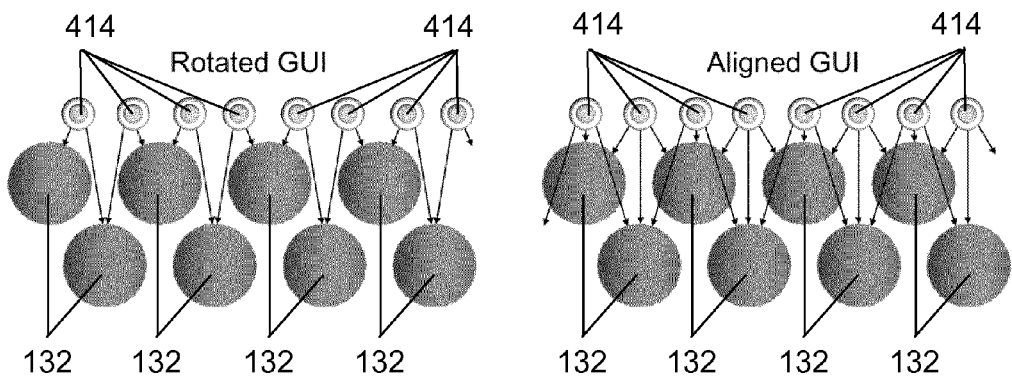
Figure 16:
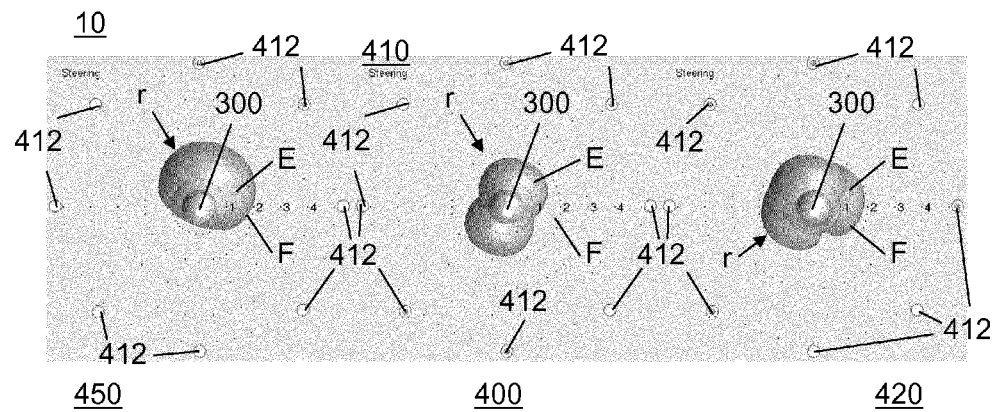
Figure 17:
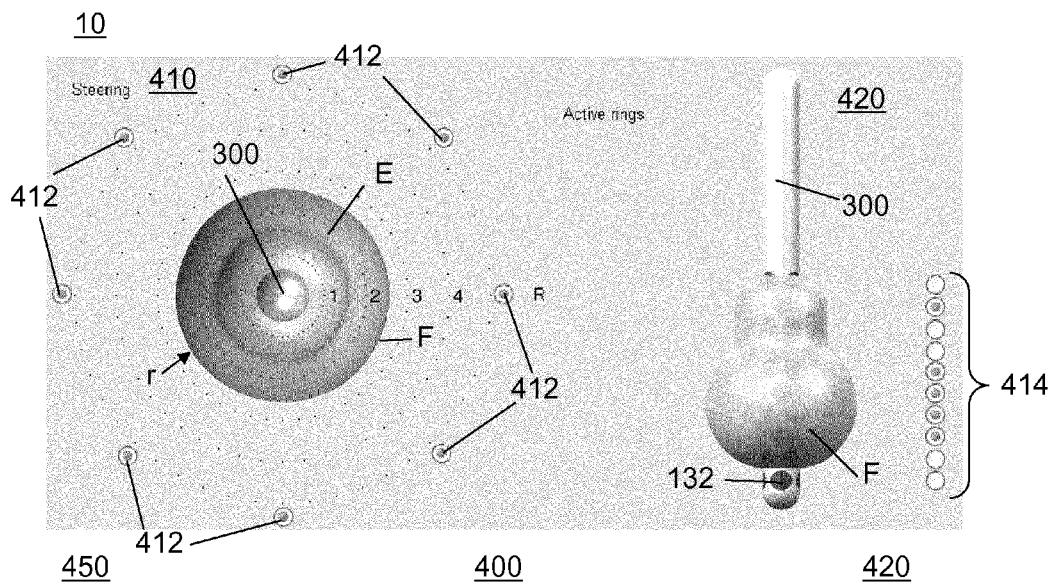
Figure 18:
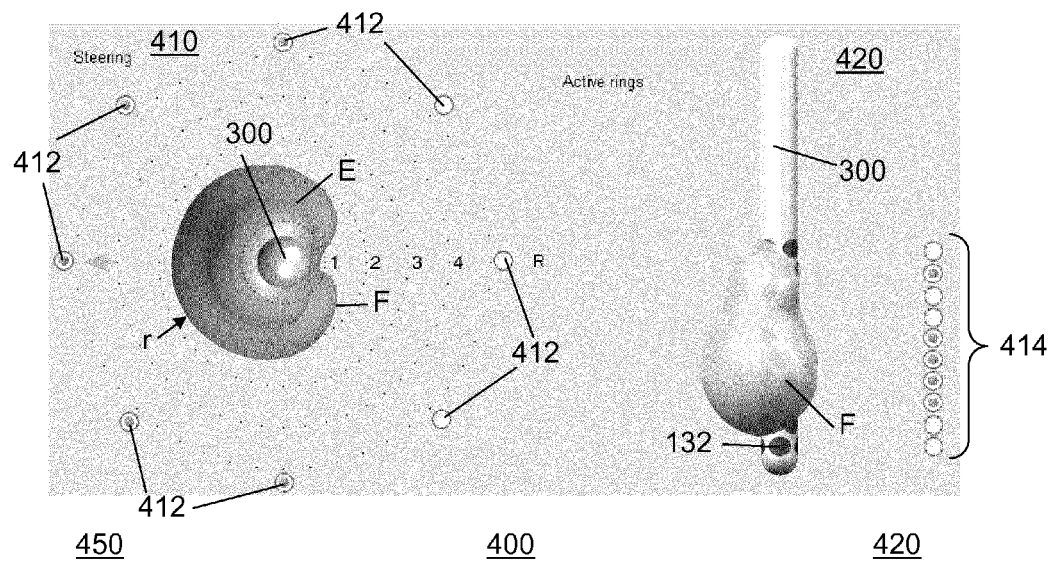
Figure 19:
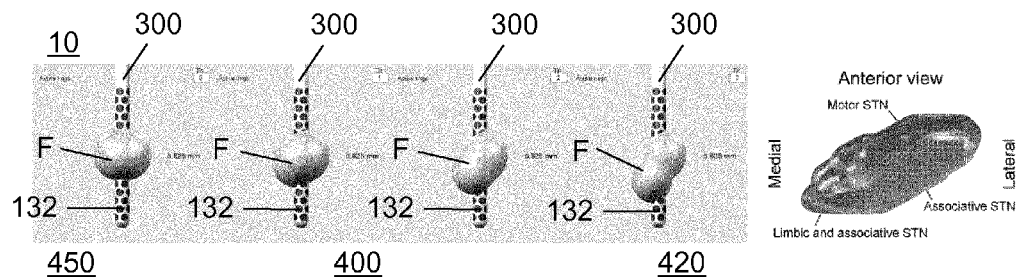
Figure 20:
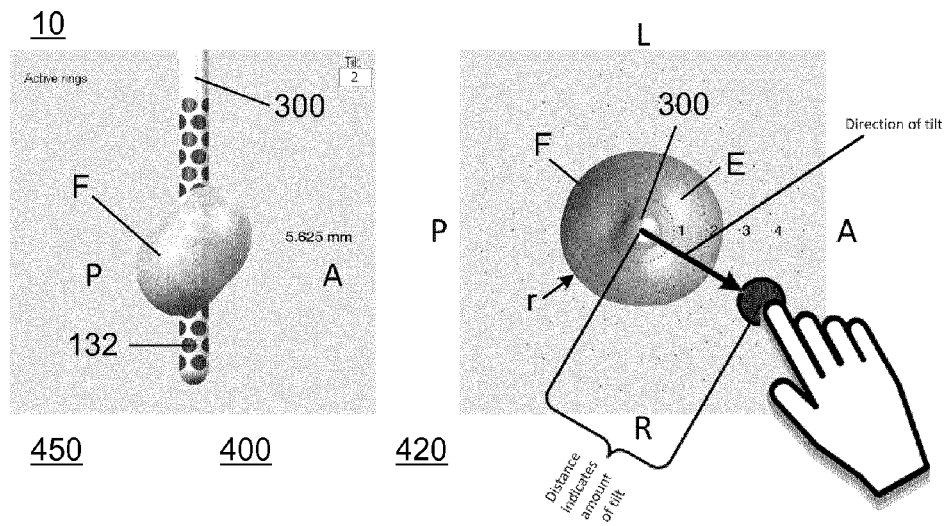
Figure 21:
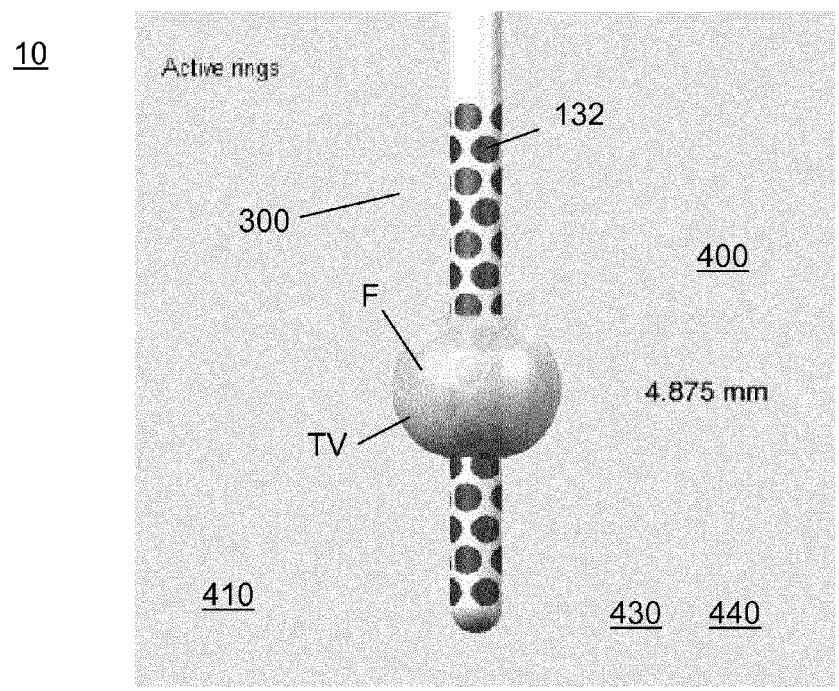
Figure 22A:
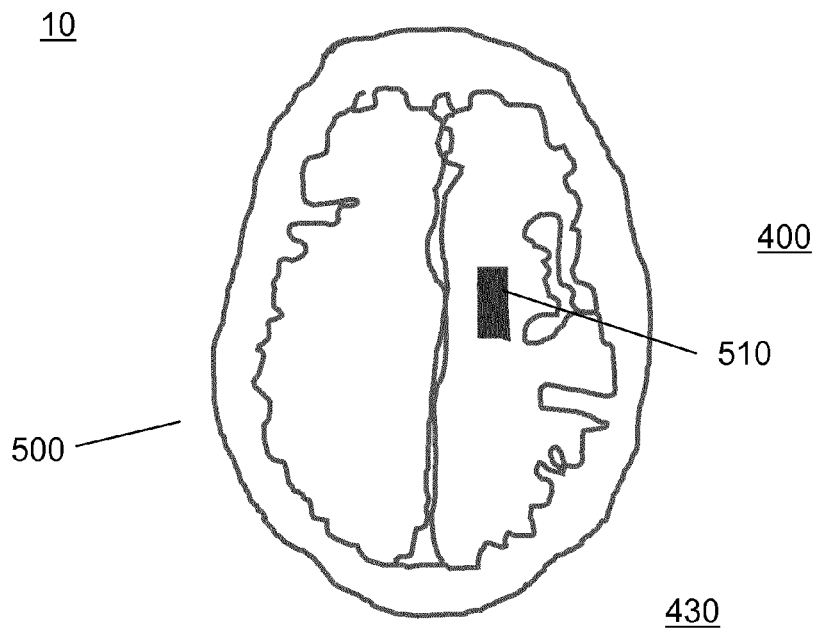
Figure 22B:
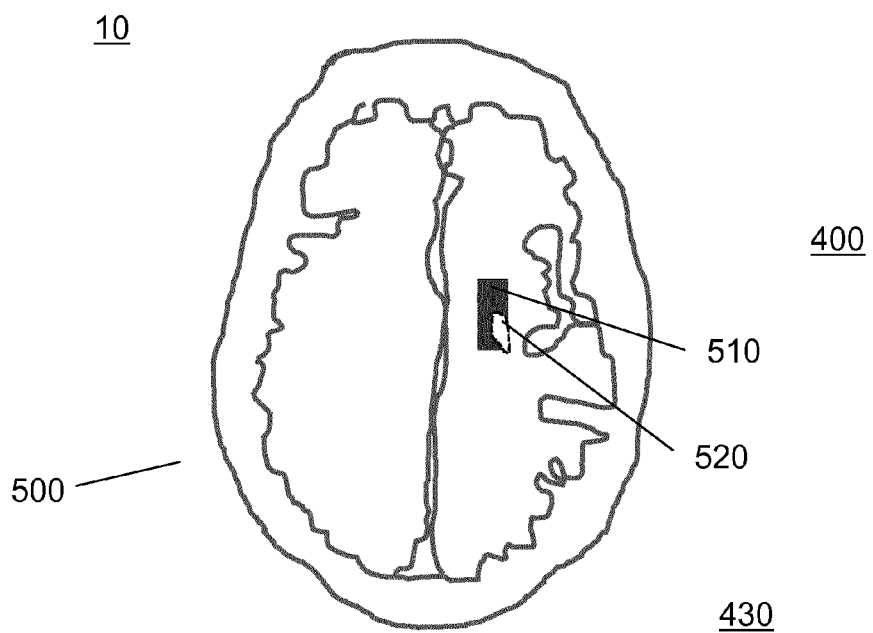
Figure 22C:
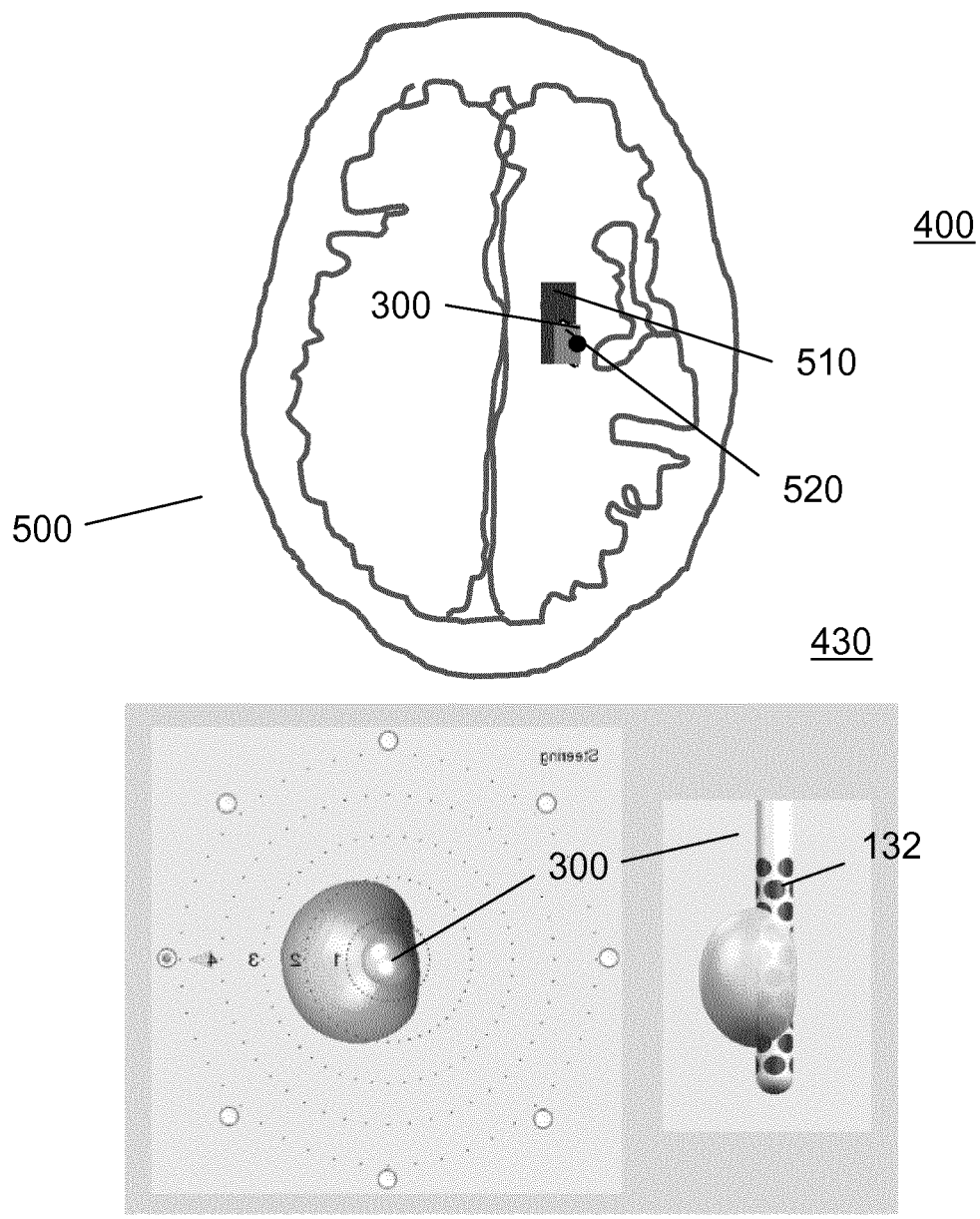

Further details and advantages of the present invention shall be described hereinafter with respect to the drawings:

FIG. 1: a schematical drawing of a neurostimulation system for deep brain stimulation (DBS);

FIG. 2: a further schematical drawing of a probe of a neurostimulation system for deep brain stimulation (DBS) and its components;

FIG. 3: a schematical drawing of a probe system according to the present invention;

FIG. 4: a first overview of a possible embodiment the system according to the invention;

FIG. 5: a second overview of a possible embodiment the system according to the invention;

FIG. 6: an overview of a possible embodiment of the system according to the first alternative system for planning and/or providing a therapy for neural applications;

Figures 7, 8:
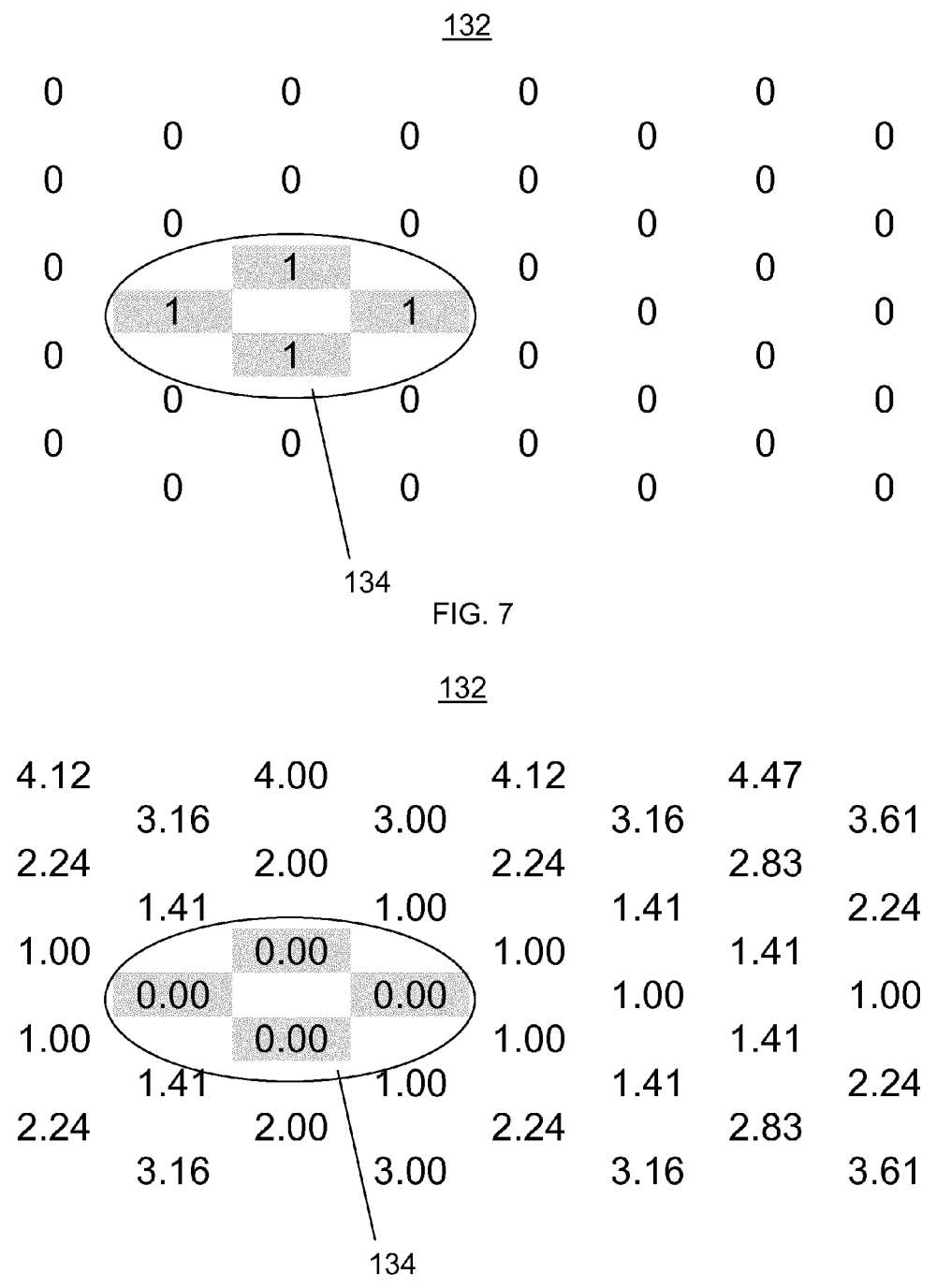

FIG. 7: a schematical and abstract overview of an array of electrodes in connection with the second alternative system;

FIG. 8: a further schematical and abstract overview of an array of electrodes in connection with the second alternative system;

FIG. 9: an overview of a possible embodiment of the second alternative system;

FIG. 10: a steering system according to the prior art related to the third alternative;

FIG. 11: a side (anterior) view of a simulated electrical field around a lead related to the third alternative;

FIG. 12: a top (superior) view of a simulated electrical field around a lead related to the third alternative;

FIG. 13: a top (superior) view of a simulated electrical field around a lead provided by a system according to an embodiment related to the third alternative;

FIG. 14: a side view of the distal end of the lead with the complex array of electrodes related to the third alternative;

FIG. 15: a rotated graphical user interface and an aligned graphical user interface of the system according to an embodiment related to the third alternative;

FIG. 16: a view of the graphical user interface of the system according to an embodiment related to the third alternative;

FIG. 17: a further view of the graphical user interface of the system according to an embodiment related to the third alternative;

FIG. 18: a further view of the graphical user interface of the system according to an embodiment related to the third alternative;

FIG. 19: a first view of the graphical user interface of the system according to an embodiment related to the third alternative during tilting;

FIG. 20: a second view of the graphical user interface of the system according to an embodiment related to the third alternative during tilting;

FIG. 21: a possible embodiment of the system 10 according to the fourth alternative; and FIG. 22a-c: step a)-c) how the planning is conducted according to the fourth alternative.

A possible embodiment of a neurostimulation system 100 for deep brain stimulation (DBS) is shown in FIG. 1. The neurostimulation system 100 comprises at least a controller 110 that may be surgically implanted in the chest region of a patient 1, typically below the clavicle or in the abdominal region of a patient 1. The controller 110 can be adapted to supply the necessary voltage pulses. The typical DBS system 100 may further include an extension wire 120 connected to the controller 110 and running subcutaneously to the skull, preferably along the neck, where it terminates in a connector. A DBS lead arrangement 130 may be implanted in the brain tissue, e.g. through a burr-hole in the skull.

FIG. 2 further illustrates a typical architecture for a Deep Brain Stimulation probe 130 that comprises a DBS lead 300 and an Advanced Lead Can element 111 comprising electronic means to address electrodes 132 on the distal end 304 of the thin film 301, which is arranged at the distal end 313 and next to the distal tip 315 of the DBS lead 300. The lead 300 comprises a carrier 302 for a thin film 301, said carrier 302 providing the mechanical configuration of the DBS lead 300 and the thin film 301. The thin film 301 may include at least one electrically conductive layer, preferably made of a biocompatible material. The thin film 301 is assembled to the carrier 302 and further processed to constitute the lead element 300. The thin film 301 for a lead is preferably formed by a thin film product having a distal end 304, a cable 303 with metal tracks and a proximal end 310. The proximal end 310 of the thin film 301 arranged at the proximal end 311 of the lead 300 is electrically connected to the Advanced Lead Can element 111. The Advanced Lead Can element 111 comprises the switch matrix of the DBS steering electronics. The distal end 304 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

FIG. 3 shows schematically and in greater detail an embodiment of a system 100 for brain applications, here for neurostimulation and/or neurorecording as a deep brain stimulation system 100 as shown in FIGS. 1 and 2. The probe system 100 comprises at least one probe 130 for brain applications with stimulation and/or recording electrodes 132, whereby e.g. 64 electrodes 132 can be provided on outer body surface at the distal end of the probe 130. By means of the extension wire 120 pulses P supplied by controller 110 can be transmitted to the Advanced Lead Can 111. The controller 110 can be an implantable pulse generator (IPG) 110.

In FIG. 4 a first overview of a possible embodiment of the system 10 according to the invention is illustrated.

The system 10 is a system for planning and/or providing a therapy for neural applications, here a system 10 for neurostimulation and/or neurorecording applications, namely a system 10 for planning and providing deep brain stimulation therapy.

The system 10 comprises a lead 300 having a plurality of electrodes 132. The electrodes 132 are capable to provide at least one stimulation field F; F1; F2.

The plurality of electrodes 132 forms a complex geometrical array and the plurality of electrodes 132 is arranged circumferentially around at least one section of the lead, here around a section next to the distal tip end of the lead 300.

The system 10 further comprises at least one adjustment means 400, the adjustment means 400 being configured such that at least one characteristic parameter of the stimulation field F; F1; F2 is directly and/or indirectly adjusted in order to establish at least one stimulation field F; F1; F2 with at least one user defined maximal stimulation field characteristic at at least one user defined radial distance away from the lead 300.

The adjustment means 400 is configured such that the stimulation field F; F1; F2 is automatically adjusted. The at least one stimulation field characteristic may be the activation of neurons caused by the at least one stimulation field F; F1; F2 and/or the field strength of the at least one stimulation field F; F1; F2.

The at least one characteristic parameter of the stimulation field F; F1; F2 may be the stimulation amplitude and/or stimulation energy and/or the pulse-width.

The adjustment means 400 includes at least one input means 410 for inputting the at least one characteristic parameter of the stimulation field F; F1; F2 and at least one visualization means 420 which is configured such that the lead and the at least one stimulation field F; F1; F2 can be visualized. The visualization means 420, based on a finite element model, is configured such that the at least one stimulation field F is displayed around an axial top view of the lead 300, which longitudinal axis represents the center of the circle of input points 412. The input means 410 are realized as one or more input points 412 radially arranged around the visualization of the lead 300, referred to as radially controlled stimulation.

In order to display the desired field without having to iterate the simulation of the field using the calculated amplitude, the field is displayed with an isosurface level corresponding to the measured field strength E in the tissue. Furthermore, FIG. 4 shows how the stimulation field F is affected when additional active electrode contacts 132 are activated (from left to right column).

FIG. 5 shows a second overview of a possible embodiment the system according to the invention as disclosed by FIG. 4. Radial controlled programming is realized with several current sources to control an arbitrary stimulation field. When several sources are used the maximum stimulation field isosurface is aligned with the desired radius. The visualization is provided with an electric field isolevel.

As shown in FIGS. 4 and 5 there is a geometrical interrelation of input and visualization, i.e. the input means 410 with the input points 412 and the visualization of at least one stimulation field F; F1; F2 is geometrically interrelated.

The geometrical interrelation of input and visualization is provided such that the visualization of the lead and the visualization of at least one stimulation field is arranged in the center of the input means, here in the center of the circle of input points 412, wherein further especially the longitudinal axis of the lead 300 being displayed in an axial top view is in the center of the circle of input points 412 and the stimulation field is displayed on an isosurface level which is identical to the level defined by the input points 412.

The adjustment means 400 comprises at least one touch screen 450, wherein the touch screen 450 is configured such that the at least one input means 410 and the at least one visualization means 420 are provided by the touch screen 450. It is possible that the views shown in FIGS. 4 and 5 are displayed via the touch screen 450 and that substantially all user input may be input via the touch screen 450.

Also, the system 10 comprises a simulation means, wherein the simulation means is capable to calculate and/or to simulate a stimulation field for a unit amplitude(s) applied to a specific set of active electrode contacts defined by the user. The system 10 is configured such that the maximum electric field strength E that should be distributed at a radial distance r is defined by the user, especially via the adjustment means 400.

The system 10 is configured such that the maximum electric field strength is measured at the radial distance r in the finite element simulation, wherein especially the maximum electric field strength in the finite element simulation is measured by the simulation means and wherein especially the finite element simulation is simulated and provided by the simulation means. The simulation means is capable to calculate the ratio between the measured field strength and the desired field strength.

Furthermore, the simulation means is capable to multiply the unit amplitude(s) that was used during the simulation with the ratio between the measured field strength and the desired field strength and that the result is the amplitude required to produce the desired stimulation field.

In order to display the desired field without having to iterate the simulation of the field using the calculated amplitude, it is possible to display the field with an isosurface level corresponding to the measured field strength in the tissue. This can be done since the size and shape of that isosurface will be identical to the desired isosurface after recalculating the field with the calculated amplitude.

Radial controlled stimulation can also be used to keep a constant but unspecified maximum field radius when the active electrode contact configuration is changed. In such case the radial distance r of the stimulation field F, F1, F2 is measured in the finite element simulation generated by the previous stimulation settings. This way the stimulation field radius is kept constant to the previous stimulation field settings.

Furthermore, as a part of the present disclosure also the following details of the first alternative system for planning and/or providing a therapy for neural applications are explicitly disclosed:

FIG. 6 shows an overview of a possible embodiment of the system 10 according to the first alternative system for planning and/or providing a therapy for neural applications.

The system 10 is a system 10 for planning and/or providing a therapy for neural applications, in this embodiment a system 10 for neurostimulation and/or neurorecording applications, here for deep brain stimulation.

The lead 300 has a plurality of electrodes 132 which forms a complex geometrical array and/or that the plurality of electrodes 132 is arranged circumferentially around at least one section of the lead, especially around a section next to the distal tip end of the lead 300.

The processing means 400 is capable to calculate and to determine and to process characterizing data of a stimulation field being provided by the electrodes 132 comprising at least two different field components. The at least two different field components are a first field component FC1 having a first field vector and a second field component FC2 having a second field vector having a second field vector different from the first field vector. The processing means 400 is further configured such that the directional component of the stimulation field F may be determined.

The field vector may define the direction of the electric field, i.e. e.g. the stimulation field. The direction of the electric field may be defined by the force that is exerted on a positively charged particle.

Here, the first field component FC1 is an anodic field component and the second field component FC2 is a cathodic field component. The cathodic field component is provided by at least one (or more) electrode(s) 132 through which e.g. electric current flows out. The anodic field component is provided by at least one (or more) electrode(s) 132 through which e.g. electric current "flows in".

So, the first field component FC1 is a field component having a field vector pointing away from the lead 300 and the second field component FC2 is a field component having a field vector pointing towards from the lead 300.

The processing means 400 is configured such that the directional component of the stimulation field F is determined by determining and/or analysing the location L and the first and/or second field vector.

Two components of the location L and the first and/or second field vector are determined and are used for the determination of the directional component of the stimulation field F, especially that only the x-component and the y-component of the location L and the first and/or second field vector are determined and are used for the determination of the directional component of the stimulation field F.

The vectors and also the location, which can be considered also as a vector, may comprise a x-component, a y-component and a z-component. For instance, in a case, where the longitudinal axis of the lead is located along the z-axis, only the x-component and the y-component are to be considered.

By this, the advantage is achieved that the determination process is simplified and thus accelerated. Further, the determination process requires less calculation capability of the processing means and also less storage capability of the processing means. Additionally, by this the determination problem is reduced from a 3D-problem and 3D-calculation to a 2D-calculation.

Further, the processing means 400 is configured such that the dot product of the location L and the first and/or second field vector is determined, wherein especially it is determined that the first field component FC1 is a field component having a field vector pointing away from the lead 300 if the dot product is >0, i.e. has a value larger than zero, and the second field component (FC2) is a field component having a field vector pointing towards from the lead (300) is <0, i.e. has a value lower than zero.

For example, in order to define a stimulation field as anodic or cathodic, the stimulation field vectors together with their locations are considered. In the case when the stimulation field is an electric field F, assume we have an electric field vector, E:

$$E = \begin{pmatrix} a \\ b \\ c \end{pmatrix}$$

The electric field F is located at coordinate (x, y, z) and the DBS lead 300 is located along the z-axis at (0, 0, z). The location L of the vector (x, y, z) may also be considered a vector. In order to decide if the electric field vector is pointing towards the lead 300 or away from the lead 300, the angle between the location vector and the vector itself is regarded. The dot product of two Euclidian vectors is directly related to the cosine of the angle between the vectors. In order to decide if a vector is pointing towards the lead or away from the lead we only need to consider the x and y components of the vectors, given that the lead is located along the z-axis. If the angle between the two vectors is smaller than $\pi/2$ radians (90 degrees) we know that the vector is pointing away from the lead and towards the lead otherwise. In our case it is not important to know the exact angle only that it is larger or smaller than 90 degrees. The dot product of two vectors are >0 if the angle is smaller than 90 degrees, and <0 if the angle is larger than 90 degrees. Thus, we defined the cathodic field as the vectors for which the dot product of the field vector and the coordinate vector is <0. In order to display the electric field with a 3D isosurface, or a colour-coded field map, the magnitude of each field vector must be calculated. This is done with Pythagoras theorem:

$$|a| = \sqrt{a_x^2 + a_y^2 + a_z^2}$$

Where a is a vector and $a_i$ the different components of the vector.

An example of electric fields and cathodic fields produced by the same electrical settings are shown in FIG. 6. The distribution of the stimulation fields as produced by a neurostimulator device 100 were visualized e.g. with a touch screen with electric fields (e.g. green) shown in the left column, cathodic fields (e.g. red) in the middle column, at an isolevel at 400 V/m. The electrical settings used to produce the fields were displayed with an unfolded contact array in the right column where purple refers to contacts that are grounded, and e.g. yellow displayed contacts that have a negative electric potential.

Especially, in connection with the first alternative system for planning and/or providing a therapy for neural applications the following aspects are explicitly disclosed:

1. A system for planning and/or providing a therapy for neural applications, especially for neurostimulation and/or neurorecording applications, comprising at least one lead (300), the lead (300) having a plurality of electrodes (132), further comprising a processing means (400) being capable to calculate and/or to determine and/or to process characterizing data of a stimulation field (F) being provided by the electrodes (132), the characterizing data of the stimulation field (F) comprising at least two different field components (FC1; FC2), wherein the at least two different field components are a first field component (FC1) having a first field vector and a second field component (FC2) having a second field vector having a second field vector different from the first field vector, wherein the processing means (400) is further configured such that the directional component of the stimulation field (F) may be determined based on the characterizing data of the stimulation field (F).

2. The system (10) according to aspect 1 of the first alternative system, wherein the plurality of electrodes (132) forms a complex geometrical array and/or that the plurality of electrodes (132) is arranged circumferentially around at least one section of the lead, especially around a section next to the distal tip end of the lead (300).

3. The system (10) according to aspect 1 or 2 of the first alternative system, wherein the first field component (FC1) is an anodic field component and the second field component (FC2) is a cathodic field component.

4. The system (10) according to one of the preceding aspects of the first alternative system, wherein the first field component (FC1) is a field component having a field vector pointing away from the lead (300) and the second field component (FC2) is a field component having a field vector pointing towards from the lead (300).

5. The system (10) according to one of the preceding aspects of the first alternative system, wherein the processing means (400) is configured such that the directional component of the stimulation field (F) is determined directly and/or indirectly by determining and/or analysing the location (L) and the first and/or second field vector.

6. The system (10) according to according to aspect 5 of the first alternative system, wherein the processing means (400) is configured such that two components of the location (L) and the first and/or second field vector are determined and are used for the determination of the directional component of the stimulation field (F), especially that only the x-component and the y-component of the location (L) and the first and/or second field vector are determined and are used for the determination of the directional component of the stimulation field (F).

7. The system (10) according to one of the preceding aspects of the first alternative system, wherein the processing means (400) is configured such that the dot product of the location (L) and the first and/or second field vector is determined, wherein especially it is determined that the first field component (FC1) is a field component having a field vector pointing away from the lead (300) if the dot product is >0, i.e. has a value larger than zero, and the second field component (FC2) is a field component having a field vector pointing towards from the lead (300) if the dot product is <0, i.e. has a value lower than zero.

8. A system for neural applications (100), especially a system for neurostimulation and/or neurorecording applications (100), for instance a deep brain stimulation system (100), the system for neural applications (100) comprising at least one system (10) for planning and/or providing a therapy for neural applications according to one of the preceding aspects of the first alternative system.

9. A method for determining the directional component of a stimulation field (F) provided by the electrodes (132) of a lead (300) based on characterizing data of the stimulation field (F), wherein the lead (300) is a lead (300) for neural applications, especially for neurostimulation and/or neurorecording applications, wherein the characterizing data of the stimulation field (F) comprising at least two different field components are calculated and/or determined and/or processed, wherein the at least two different field components are a first field component (FC1) having a first field vector and a second field component (FC2) having a second field vector having a second field vector different from the first field vector.

10. The method according to aspect 9 of the first alternative system, wherein the plurality of electrodes (132) forms a complex geometrical array and/or that the plurality of electrodes (132) is arranged circumferentially around at least one section of the lead, especially around a section next to the distal tip end of the lead (300).

11. The method according to aspect 9 or 10 of the first alternative system, wherein the first field component (FC1) is an anodic field component and the second field component (FC2) is a cathodic field component and/or the first field component (FC1) is a field component having a field vector pointing away from the lead (300) and the second field component (FC2) is a field component having a field vector pointing towards from the lead (300).

12. The method according to one of aspects 9 to 11 of the first alternative system, wherein the directional component of the stimulation field (F) is determined directly and/or indirectly by determining and/or analysing the location (L) and the first and/or second field vector.

13. The method according to one of aspects 9 to 12 of the first alternative system, wherein two components of the location (L) and the first and/or second field vector are determined and are used for the determination of the directional component of the stimulation field (F), especially that only the x-component and the y-component of the location (L) and the first and/or second field vector are determined and are used for the determination of the directional component of the stimulation field (F).

14. The method according to one of aspects 9 to 13 of the first alternative system, wherein the dot product of the location (L) and the first and/or second field vector is determined, wherein especially it is determined that the first field component (FC1) is a field component having a field vector pointing away from the lead (300) if the dot product is >0, i.e. has a value larger than zero, and the second field component (FC2) is a field component having a field vector pointing towards from the lead (300) if the dot product is <0, i.e. has a value lower than zero.

15. The method according to one of aspects 9 to 14 of the first alternative system, wherein the method is conducted with at least one system (10) for planning and/or providing a therapy for neural applications according to one of aspects 1 to 7 of the first alternative system and/or a system for neural applications (100) according to aspect 8 of the first alternative system.

Furthermore, as a part of the present disclosure also the following details of the second alternative system for planning and/or providing a therapy for neural applications are explicitly disclosed:

FIG. 7 shows a schematical and abstract overview of an (unfolded) array of electrodes 132, here 8 columns of electrodes 132 and 10 rows of electrodes 132.

The plurality of electrodes 132 forms a complex geometrical array and the plurality of electrodes 132 is arranged circumferentially around at least one section of the lead, here around a section next to the distal tip end of the lead 300.

Gradual focused stimulation can be achieved by grounding contacts of electrodes 132 at a varying distance from the active contact 134. The active contact 134 may be at least one (or also a plurality of several electrodes 132) which is active and which is "stimulating" the tissue next and/or adjacent to the electrode 132 and lead 300. The active contact 134 may be also named as cathode, i.e. at least one electrode 132 through which e.g. electric current flows out of the electrode.

In order to obtain a strong focusing effect on the stimulation field F (see e.g. FIG. 9) it is essential that the grounded contacts are located close to the active contact(s) 134, e.g. the cathode(s).

In the current concept, full focusing effect is generated by automatically grounding contacts adjacent to the active contact 134. When a lower amount of focus is desired, electrodes 132 further away from the active contact 134 are grounded, see FIG. 7. In FIG. 4, "1" refers to active electrodes 132 and form the active contact 134 and "0" refer to inactive electrodes.

In order to decide what contacts should be grounded to obtain a certain amount of focusing a distance transformation of all the active electrode contacts may be used.

FIG. 8 is a simple example of how the distance transformation is used.

The Euclidian distance between every electrode 132 to the active electrodes 132 forming the active contact 134 can then be calculated with a distance transformation.

The numbers representing each electrode 132 reflect the Euclidian distance to the active contact 134. In this example the distances are ranging from about 4 to 1. Thus, the amount of levels that could be used for gradual adjustment of the focusing is 4. During the lowest grade of focusing the contacts with a distance of about 4 would be grounded. During the highest grade of focusing the electrodes 132 with a distance of about 1 would be grounded.

In order to make sure that the charge density safety limit is not reached when focused stimulation is turned on, the total surface area of all the grounded electrodes 132 is related to the amount of delivered current, and the number of grounded electrodes 132 may be adjusted accordingly. If the number of electrodes 132 is low in comparison to the charge density safety limit, additional electrodes may be grounded. This might be needed since all the current that is delivered by the active contact 134 will also flow through the grounded electrodes 132.

In FIG. 9 a first overview of a possible embodiment of the system 10 according to the second alternative system is illustrated.

The system 10 is a system for planning and/or providing a therapy for neural applications, here a system 10 for neurostimulation and/or neurorecording applications, namely a system 10 for planning and providing deep brain stimulation therapy.

The system 10 comprises a lead 300 having a plurality of electrodes 132. The electrodes 132 are capable to provide at least one stimulation field F.

At least one electrode 132 is capable to form an active contact 134, wherein the system 10 comprises at least one electrode potential adjusting means 400 which is configured such that electrodes 132 at varying distances from the active contact 134 may be provided with a different potential as the active contact 134 for the purpose of focusing the stimulation field F provided by the active contact 134.

The plurality of electrodes 132 forms a complex geometrical array and the plurality of electrodes 132 is arranged circumferentially around at least one section of the lead, especially around a section next to the distal tip end of the lead 300.

The electrode potential adjusting means 400 is configured such that at least one selected electrode 136 at (a) varying distance(s) from the active contact 134 may be provided with a second potential different from the first potential of the active contact 134 for the purpose of focusing the stimulation field (F) provided by the active contact 134 automatically and/or semi-automatically. The different potential as the active contact 134 may be provided by providing and/or setting at least one electrode 132 which is not a part of the active contact 134 (to) a different polarity as the active contact 134 and/or by grounding at least one electrode 132 which is not a part of the active contact 134.

Further, the electrode potential adjusting means 400 is configured such that at least one electrode 136 at (a) varying distance(s) from the active contact 134 may be provided with at least one second potential different from the potential of the active contact 134 for the purpose of focusing the stimulation field provided by the active contact 134 in a first manner and that at least one electrode 136 at (a) varying distance(s) from the active contact 134 may be provided with at least one third potential different from the potential of the active contact 134 for the purpose of focusing the stimulation field provided by the active contact 134 in a second manner.

The second potential different from the potential of the active contact 134 leads higher amount of focussing by setting at least one electrode 136 next and/or adjacent from the active contact 134 and the electrode(s) 136 set for the second manner and that the third potential different from the potential of the active contact 134 leads lower amount of focussing by setting at least one electrode 136 further away from the active contact 134 and the electrode(s) 136 set for the first manner.

The electrodes next and/or adjacent from the active contact may be electrodes forming a ring around the active contact. The electrodes further away from the active contact may be electrodes which are e.g. not part of the ring around the active contact.

Moreover, the electrode potential adjusting means 400 is capable to calculate the Euclidian distance between at least one of the electrodes not belonging to the active contact 134, wherein especially the Euclidian distance between at least one of the electrodes not belonging to the active contact 134 is calculated by means of a distance calculation (see also e.g. FIG. 8).

By this, the advantage can be achieved that a mathematically based and thus exact determination of the electrodes to be changed regarding their potential can be provided.

The total surface area of all electrodes 132, 136 with a potential different from the potential of the active contact 134 is related to the amount of delivered current and the number of electrodes 132, 136 with a potential different from the potential of the active contact 134 is adjusted according to a predetermined safety threshold value such that the charge density safety limit is not reached when focused stimulation is turned on.

By this, the advantage is achieved that the safety of the system may be increased. In particular, by this it is possible to assure that the charge density safety limit is not reached when focused stimulation is turned on, since the total surface area of e.g. all the grounded electrodes or electrodes with a different polarity is related to the amount of delivered current and the number of grounded electrodes or electrodes with a different polarity may be then adjusted accordingly.

The different potential may be gradually and/or stepwise decreased and/or increased.

As can been further see in FIG. 9 in the far left column, the distribution of the stimulation fields F as produced by a neurostimulator device 100 with the lead 300 is visualized with cathodic electrical fields (e.g. in red), at an isolevel of 400 V/m. The focusing effect is gradually increased from top to bottom by grounding contacts closer to the cathodes. In the middle left column, the electrical settings used to produce the fields F displayed with an unfolded contact array where blue refers to contacts that are grounded, and red displays cathodes are shown. In the middle right column it is shown how grounding can be applied during steering stimulation. The focusing effect is gradually increased from top to bottom. In the right column it is shown that the electrical settings used to produce the fields displayed with an unfolded contact array.

Especially, in connection with the second alternative system for planning and/or providing a therapy for neural applications the following aspects are explicitly disclosed:

1. A system (10) for planning and/or providing a therapy for neural applications, especially for neurostimulation and/or neurorecording applications, comprising at least one lead (300), the lead (300) having a plurality of electrodes (132), at least one electrode (132) being capable to form an active contact (134) with a first potential, wherein the system (10) comprises at least one electrode potential adjusting means (400) which is configured such that at least one selected electrode (136) at (a) varying distance(s) from the active contact (134) may be provided with a second potential different from the first potential of the active contact (134) for the purpose of focusing the stimulation field (F) provided by the active contact (134).

2. The system (10) according to aspect 1 of the second alternative system, wherein the plurality of electrodes (132) forms a complex geometrical array and/or that the plurality of electrodes (132) is arranged circumferentially around at least one section of the lead, especially around a section next to the distal tip end of the lead (300), and/or that the electrode potential adjusting means (400) is configured such that at least one selected electrode (136) at (a) varying distance(s) from the active contact (134) may be provided with a second potential different from the first potential of the active contact (134) for the purpose of focusing the stimulation field (F) provided by the active contact (134) automatically and/or semi-automatically.

3. The system (10) according to aspect 1 or 2 of the second alternative system, wherein the system (10) is configured such that the second potential may be provided by providing and/or setting at least one electrode (136) which is not a part of the active contact (134) (to) a second polarity different from the first polarity of the active contact (134) and/or by grounding at least one electrode (136) which is not a part of the active contact (134), wherein especially the electrode potential adjusting means (400) is configured such that the second potential may be provided by providing and/or setting at least one electrode (136) which is not a part of the active contact (134) (to) a second polarity different from the first polarity of the active contact (134) and/or by grounding at least one electrode (136) which is not a part of the active contact (134).

4. The system (10) according to one of the preceding aspects of the second alternative system, wherein the electrode potential adjusting means (400) is configured such that at least one electrode (136) at (a) varying distance(s) from the active contact (134) may be provided with at least one second potential different from the potential of the active contact (134) for the purpose of focusing the stimulation field provided by the active contact (134) in a first manner and that at least one electrode (136) at (a) varying distance(s) from the active contact (134) may be provided with at least one third potential different from the potential of the active contact (134) for the purpose of focusing the stimulation field provided by the active contact (134) in a second manner.

5. The system (10) according to aspect 4 of the second alternative system, wherein the second potential different from the potential of the active contact (134) leads higher amount of focussing by setting at least one electrode (136) next and/or adjacent from the active contact (134) and the electrode(s) (136) set for the second manner and that the third potential different from the potential of the active contact (134) leads lower amount of focussing by setting at least one electrode (136) further away from the active contact (134) and the electrode(s) (136) set for the first manner.

6. The system (10) according to one of the preceding aspects of the second alternative system, wherein the electrode potential adjusting means (400) is configured such that the Euclidian distance between at least one of the electrodes not belonging to the active contact (134) is calculated, wherein especially the Euclidian distance between at least one of the electrodes not belonging to the active contact (134) is calculated by means of a distance calculation.

7. The system (10) according to one of the preceding aspects of the second alternative system, wherein the electrode potential adjusting means (400) is configured such that the total surface area of all electrodes (132; 136) with a potential different from the potential of the active contact (134) is related to the amount of delivered current and the number of electrodes (132; 136) with a potential different from the potential of the active contact (134) is adjusted according to a predetermined safety threshold value such that the charge density safety limit is not reached when focused stimulation is turned on.

8. The system (10) according to one of the preceding aspects of the second alternative system, wherein the electrode potential adjusting means (400) is configured such that the potential different from the potential of the active contact (134) may be gradually and/or stepwise decreased and/or increased.

9. A system for neural applications (100), especially a system for neurostimulation and/or neurorecording applications (100), for instance a deep brain stimulation system (100), the system for neural applications (100) comprising at least one system (10) for planning and/or providing a therapy for neural applications according to one of the preceding aspects of the second alternative system.

10. A method for focusing the stimulation field provided by an active contact (134) of a lead (300), wherein the lead (300) comprises a plurality of electrodes (132), at least one electrode (132) being capable to form an active contact (134), wherein the method comprises at least the step of providing electrodes (136) at varying distances from the active contact (134) with a second potential different from the first potential of the active contact (134) for the purpose of focusing the stimulation field (F) provided by the active contact (134).

11. The method of aspect 10 of the second alternative system, wherein the different potential as the active contact (134) is provided by providing and/or setting at least one electrode (136) which is not a part of the active contact (134) (to) a second polarity different from the first polarity of the active contact (134) and/or by grounding at least one electrode (136) which is not a part of the active contact (134).

12. The method of aspect 10 or 11 of the second alternative system, wherein at least one electrode (136) at (a) varying distance(s) from the active contact (134) may be provided with at least one second potential different from the potential of the active contact (134) for the purpose of focusing the stimulation field provided by the active contact (134) in a first manner and that at least one electrode (136) at (a) varying distance(s) from the active contact (134) may be provided with at least one third potential different from the potential of the active contact (134) for the purpose of focusing the stimulation field provided by the active contact (134) in a second manner, wherein in particular the second potential different from the potential of the active contact (134) leads to a higher amount of focussing by setting at least one electrode (136) next and/or adjacent from the active contact (134) and the electrode(s) (136) set for the second manner and that the third potential different from the potential of the active contact (134) leads to a lower amount of focussing by setting at least one electrode (136) further away from the active contact (134) and the electrode(s) (136) set for the first manner.

13. The method according to one of aspects 10 to 12 of the second alternative system, wherein the Euclidian distance between at least one of the electrodes not belonging to the active contact (134) is calculated, wherein especially the Euclidian distance between at least one of the electrodes not belonging to the active contact (134) is calculated by means of a distance calculation.

14. The method according to one of aspects 10 to 13 of the second alternative system, wherein the total surface area of all electrodes (132) with a potential different from the potential of the active contact (134) is related to the amount of delivered current and the number of electrodes (132) with a potential different from the potential of the active contact (134) is adjusted according to a predetermined safety threshold value such that the charge density safety limit is not reached when focused stimulation is turned on.

15. The method according to one of aspects 11 to 14 of the second alternative system, wherein the method is conducted with at least one system (10) for planning and/or providing a therapy for neural applications according to one of aspects 1 to 9 of the second alternative system and/or a system for neural applications (100) according to aspect 10 of the second alternative system.

Furthermore, as a part of the present disclosure also the following details of the third alternative system for planning and/or providing a therapy for neural applications are explicitly disclosed:

FIG. 10 shows steering system according to the prior art. This known system provides a steering functionality are commonly controlled with buttons that are organized in a joystick like manner. With a joystick control JC the stimulation field F is moved asymmetrically around the centre of the lead. However, moving the field F into a certain direction may from a clinical point of view not be the most intuitive way of controlling the field F during neurostimulation. It may be hypothesised that steering is primarily going to be used when unwanted stimulation-induced side-effects are encountered. In such case it is hypothesised that the user would like to turn off certain parts of the field F in the anatomical direction where the side effect is suspected to be related, rather than moving the field away from a certain direction where the field will enter new tissue in the opposite direction. Another limitation of the joystick approach is that the field F can only be steered in one direction at a time.

FIGS. 11 and 12 show a side (anterior; FIG. 11) and top (superior; FIG. 12) view of simulated electric fields F with around the lead 300 during a) no steering, b) steering by moving the field with joystick controls, and c) steering by turning off certain parts of the field. The electric fields F may be visualized with coloured (e.g. green) isolevels in 3D, and black and grey contours in 2D at a threshold of e.g. 400 V/m.

The electric field strength E of the Field F may be measured at the radial distance r.

In a possible embodiment of the third alternative a system 10 may be a system 10 for planning and/or providing a therapy for neural applications, especially for neurostimulation and/or neurorecording applications, here a system 10 for planning and/or providing a deep brain stimulation (DBS) therapy. This system 10 may realize a graphical user interface concept for neurostimulator devices that allows steering of the stimulation field in multiple directions simultaneously.

In particular, the system 10 comprises at least one lead 300. The lead 300 has a plurality of electrodes 132 being capable to provide at least one stimulation field F. The plurality of electrodes 132 forms a complex geometrical array and/or that the plurality of electrodes 132 is arranged circumferentially around at least one section of the lead, especially around a section next to the distal tip end of the lead 300.

The complex array is formed by a plurality of electrodes 132, which are arranged circumferentially around a section next to the distal tip end of the lead 300 as shown in FIG. 11. The electrodes may be e.g. arranged non-planar and non-coaxial and likewise a leopard pattern and may form a regular array. Several electrodes may form at one level a ring around the lead and the next ring may be slightly displaced such that e.g. one electrode of the second ring is partially arranged within the gap between to electrodes of the first ring. So, there are rings of electrodes in radial/circumferential direction of the lead and columns of electrodes in axial direction of the lead.

Further, the system 10 comprises an adjustment means 400 being capable to adjust the stimulation field in multiple directions and a steering means 410 being capable to steer the stimulation field in multiple directions simultaneously. The adjustment means 400 is configured such that the shape of the at least one stimulation field F can be modelled such that user input via the steering means 410 is transformed into the shape of the stimulation field F. Further, the adjustment means 400 is configured such that the shape of the stimulation field F can be transformed into stimulation settings to provide the at least one stimulation field F with the electrodes 132 of the lead 300. Also, the adjustment means 400 is configured such that the stimulation field F is automatically directly and/or indirectly adjusted.

The adjustment means 400 has a touch screen 450, wherein the touch screen 450 is configured such that the steering means 410 and the visualization means 420 are provided by the touch screen 450.

The visualization means 420 is configured such that the lead 300 and the at least one stimulation field F can be visualized, wherein the steering means 410 and the visualization means 420 are interconnected such that a geometrical interrelation of input and visualization is provided. It is possible that the lead 300 is represented with or without an electrode array representation. By not displaying the electrodes of the lead the user may be not focussing on electrodes but more on field shaping which may help to achieve better planning and therapy results. There may be a switching means which is capable to switch between a representation of the lead with or without an electrode array representation.

As can be seen in FIG. 13, the visualization means 420 is configured such that the at least one stimulation field is displayed around an axial top view of the lead 300.

The steering means 410 comprises first input points 412 radially arranged around the visualization of the lead 300, wherein especially the first input points 412 are capable to adjust the at least one stimulation field F in radial direction.

So, an intuitive graphical user interface concept for multidirectional steering can be realized, which comprises input points 412 control buttons that are located in the vicinity of a stimulation lead 300.

The steering means 410 comprises one or more second input points 414 arranged adjacent and in this case parallel (see e.g. FIGS. 17 and 18) to the visualization of the lead 300, wherein especially the second input points 414 are capable to adjust the at least one stimulation field F in axial direction.

The first input points 412 or input buttons 412 and the second input points 414 or input buttons 414 of the steering means 410 are configured such that the first input points 412 and second input points 414 can be switched between two or more states related to at least one stimulation field characteristic.

The first input points 412 and also the second input points 414 of the steering means 410 are configured such that the first input points 412 and/or second input points 414 can be switched between two or more states related to at least one stimulation field characteristic.

The at least one stimulation field characteristic is the stimulation amplitude and/or stimulation energy and/or the pulse-width and/or parameters which are directly and/or indirectly influencing the stimulation amplitude and/or stimulation energy and/or the pulse-width.

Each button controls and influences the electrical settings of one or more lead contact columns, see FIG. 13. The number of control buttons may not necessarily be the same as the number of lead contact columns. Each control button can have two or more states related to the amount of electrical stimulation amplitude delivered at a certain lead contact column. Such states can be e.g. 'On', 'Off', 'Half', 'Quarter', or other values related to the stimulation amplitude (FIG. 10). Radial steering can be applied individually at different vertical levels by a control that states at what vertical level the steering should be applied.

Coloured buttons 412, 414 with a first colour, e.g. green buttons, refer to electrode contact columns or parts of electrode contact columns that are 'On', i.e. to electrode contacts where electric current is delivered, and coloured buttons 412, 414 with a second colour, e.g. white buttons, refer to electrode contact columns or parts of electrode contact columns that are 'Off'. There is not a direct mapping of electrode columns. In particular, if on the staggered array one ore more (but not all) button(s) are activated this may imply that a column is put 'Half-On'. By means of the buttons it may be controlled to which extent the filed in 'On' in the particular direction. The system is configured such that the location on the field is translated into a mapping of electrical energy and/or current transmitted to electrode contacts.

As can be seen in FIGS. 13 and 16 to 20, the geometrical interrelation of input and visualization is provided such that the visualization of the lead 300 and the visualization of at least one stimulation field F is arranged in the center of at least one part of the steering means 410, especially in the center of the circle of the first input points 412, wherein further especially the longitudinal axis of the lead 300 being displayed in an axial top view is in the center of the circle of input points 412 and the stimulation field is displayed on an isosurface level which is identical to the level defined by the first input points 412.

For example the second input points 414 of the steering means 410 are arranged in a first rotated arrangement to an unfolded visualization of at least one part of electrodes 132 provided by the visualization means 420 (see FIG. 15, left view) and that the first input points 412 and/or second input points 414 can be arranged in a second aligned arrangement to an unfolded visualization of at least one part of electrodes 132 provided by the visualization means 420 (see FIG. 15, right view). For example, by means of the input points 414 the stimulation amplitudes of aligned and/or adjacent contacts according to specific algorithms can be affected and adjusted.

The graphical user interface of the system 10 for multi-directional steering as shown in FIG. 16 is used to steer the stimulation field by setting the state of each control button 412 (and likewise also the buttons 414, see e.g. FIGS. 17 and 18). The number of directions in which the field can be steered simultaneously is primarily related to the number of lead contact columns, but ultimately also to the stimulation amplitudes as well as the size of the lead diameter and in multiple directions at the same time.

As shown in FIGS. 17 and 18, control buttons 414 are also located in the vicinity of the stimulation lead in the vertical plane. Such control buttons 414 influence the electrical settings of one or more lead contact rings. The number of control buttons 414 may not necessarily be the same as the number of lead contact rings. Each control button can have two or more states related to the amount of electrical stimulation amplitude delivered at a certain lead contact column. Such states can be e.g. 'On', 'Off', 'Half', 'Quarter', or other values related to the stimulation amplitude.

Radial and vertical steering may be combined to generate arbitrary stimulation field shapes of the stimulation field F.

As shown in FIGS. 19 and 20, the steering means 410 is configured such that the stimulation field F may be at least partially tilted and/or sloped and/or rotated.

In addition to radial and vertical steering there is also control for steering the field F by means of tilt. Tilt refers to shifting the active electrode contacts on one or more sides of the stimulation lead in the vertical direction. The effect is that the original field is tilted in one or more directions. This feature may become valuable e.g. when the programmer would like to tailor the stimulation field to cover the motor part of the subthalamic nucleus (STN).

FIG. 20 shows tilted stimulation fields in anterior view (left view), and superior view (right side). An example of a user interface (UI) control for tilt was in this example put in the superior viewport. The direction of tilt is illustrated by the arrow, and the magnitude of the tilt is defined by the radial extension of the arrow.

Especially, in connection with the third alternative system for planning and/or providing a therapy for neural applications the following aspects are explicitly disclosed:

1. A system (10) for planning and/or providing a therapy for neural applications, especially for neurostimulation and/or neurorecording applications, comprising at least one lead (300), the lead (300) having a plurality of electrodes (132) being capable to provide at least one stimulation field (F), further comprising at least one adjustment means (400) being capable to adjust the stimulation field in multiple directions and at least one steering means (410) being capable to steer the stimulation field in multiple directions simultaneously.

2. The system (10) according to aspect 1 of the third alternative system, wherein the adjustment means (400) is configured such that the shape of the at least one stimulation field (F) can be modelled such that user input via the steering means (410) is transformed into the shape of the stimulation field (F).

3. The system (10) according to aspect 2 of the third alternative system, wherein the adjustment means (400) is configured such that the shape of the stimulation field (F) can be transformed into stimulation settings to provide the at least one stimulation field (F) with the electrodes (132) of the lead (300).

4. The system (10) according to one of the preceding aspects of the third alternative system, wherein the adjustment means (400) is configured such that the stimulation field (F) is automatically directly and/or indirectly adjusted.

5. The system (10) according to one of the preceding aspects of the third alternative system, wherein the plurality of electrodes (132) forms a complex geometrical array and/or that the plurality of electrodes (132) is arranged circumferentially around at least one section of the lead, especially around a section next to the distal tip end of the lead (300).

6. The system (10) according to one of the preceding aspects of the third alternative system, wherein the adjustment means (400) comprises at least one visualization means (420) which is configured such that the lead and the at least one stimulation field (F) can be visualized, wherein the steering means (410) and the visualization means (420) are interconnected such that a geometrical interrelation of input and visualization is provided.

7. The system (10) according to aspect 6 of the third alternative system, wherein the visualization means (420) is configured such that the at least one stimulation field is displayed around an axial top view of the lead (300).

8. The system (10) according to one of the preceding aspects of the third alternative system, wherein the steering means (410) comprises one or more first input points (412) radially arranged around the visualization of the lead (300), wherein especially the first input points (412) are capable to adjust the at least one stimulation field (F) in radial direction.

9. The system (10) according to one of the preceding aspects of the third alternative system, wherein the steering means (410) comprises one or more second input points (414) arranged adjacent, especially parallel, to the visualization of the lead (300), wherein especially the second input points (414) are capable to adjust the at least one stimulation field (F) in axial direction.

10. The system (10) according to one of aspects 8 or 9 of the third alternative system, wherein the first input points (412) and/or second input points (414) of the steering means (410) are configured such that the first input points (412) and/or second input points (414) can be switched between two or more states related to at least one stimulation field characteristic.

11. The system (10) according to aspect 10 of the third alternative system, wherein the at least one stimulation field characteristic is the stimulation amplitude and/or stimulation energy and/or the pulse-width and/or parameters which are directly and/or indirectly influencing the stimulation amplitude and/or stimulation energy and/or the pulse-width.

12. The system (10) according to one of aspects 8 to 11 of the third alternative system, the first input points (412) and/or second input points (414) of the steering means (410) are configured such that the first input points (412) and/or second input points (414) can be arranged in a first rotated arrangement to an unfolded visualization of at least a part of electrodes (132) provided by the visualization means (420) and that the first input points (412) and/or second input points (414) can be arranged in a second aligned arrangement to an unfolded visualization of at least a part of electrodes (132) provided by the visualization means (420).

13. The system (10) according to one of the preceding aspects of the third alternative system, wherein the steering means (410) is configured such that the stimulation field (F) may be at least partially tilted and/or sloped and/or rotated.

14. The system (10) according to one of aspects 6 to 13 of the third alternative system, wherein the geometrical interrelation of input and visualization is provided such that the visualization of the lead (300) and the visualization of at least one stimulation field (F) is arranged in the center of at least a part of the steering means (410), especially in the center of the circle of the first input points (412), wherein further especially the longitudinal axial of the lead (300) being displayed in an axial top view is in the center of the circle of input points (412) and the stimulation field is displayed on an isosurface level which is identical to the level defined by the first input points (412).

15. The system (10) according to one of aspects 6 to 14 of the third alternative system, wherein the adjustment means (400) comprises at least one touch screen (450), wherein the touch screen (450) is configured such that the at least one steering means (410) and the at least one visualization means (420) are provided by the touch screen (450).

Furthermore, as a part of the present disclosure also the following details of the fourth alternative system for planning and/or providing a therapy for neural applications are explicitly disclosed:

FIG. 21 shows a system 10 for planning and/or providing a therapy for neural applications, here for neurostimulation and/or neurorecording applications, i.e. for DBS according to the fourth alternative.

The system 10 comprises at least one therapy delivery means 300, here a DBS lead 300 with a complex array of electrodes 132 being capable to influence a volume of tissue of a patient (1) (see e.g. FIG. 1) with a stimulation field F.

The shape of the volume of tissue TV that shall be influenced by the lead 300 may be modelled and the necessary settings and/or implantation conditions of lead 300 may be set accordingly and automatically.

Further, the system 10 comprises at least one processing means 410 being capable to combine specific anatomical data and/or functional data and information about the volume of tissue TV of a patient 1 that can be influenced by the lead 300, wherein the at least one steering and/or field shaping means 400 is configured such that the therapy delivered by the lead 300 may be steered depending on at least one output of the processing means 410.

A touch screen 430 is provided as visualization means 430, which is capable to visualize volume of tissue TV of a patient 1 to be addressed by the lead 300, especially in the context of the pre-operative and/or peri-operative images of the patient 1.

The visualization means 430 is configured such that at least one or more effective shape of the volume of tissue TV may be displayed and that the system 10 comprises a simulation means 440 which is capable to provide a feed-forward simulation of the shape of the volume of tissue TV that shall be provided by the at least one therapy delivery means 300 and that visualization means 430 is configured such that patient images may be combined with a feed-forward simulation of the shape of the volume of tissue TV that shall be provided by the at least one therapy delivery means 300.

The simulation means 440 is configured such that information about tissue anisotropy and/or tissue inhomogenity is used for the simulation when providing a feed-forward simulation of the shape of the volume of tissue TV that shall be provided by the at least one therapy delivery means 300.

Images of the patient 1 are loaded and the user can indicate a target volume TV, e.g. by voxel painting or by free-form drawing of 3D volumes on the patient images. The software as identifying means identifies from the indicated target volume TV a most optimal lead that generates field-shapes overlapping with the user indicated target volume TV. The selected lead is positioned automatically by the system 10 in an orientation that matches the target volume TV, or it can be placed manually by the user on the images and the target volume TV.

Alternatively and/or additionally it is possible that patient images (MRI/CT) are combined with a feed-forward simulation of electrical field(s) F than can be produced by the to-be-implanted DBS system 100. The user selects a DBS lead 300, and for this lead several "effective" volumes can be displayed (non-polarized electric field, directionally dependent electric field, neuronal activation). Volumes can be displayed in 2D by colour coding of MRI voxels (e.g. spread of electric field indicated by red voxels), or using 3D meshes. The user can position the lead 300 and its effective volumes in such a way as to give an optimal result, i.e. good overlap with the target volume TV.

Further alternatively and/or additionally it is possible that information about tissue anisotropy/inhomogenity (deduced from e.g. MRI/DTI) is taken into account in the simulation of the electric field model.

Further alternatively and/or additionally it is possible that the user identifies target area and outlines desired electrical field coverage volume. The system computes and identifies optimal lead for this and shows the lead 300 and stimulation capabilities on top of this.

Also, it is possible to extend the capabilities of the system 10 by allowing the user to provide more boundary-conditions, e.g. by demanding a certain range of lead-implantation angles, by demanding a lead position relative to the TV (e.g. lateral to the TV), by demanding certain areas to remain unaffected by stimulation, etc. Essentially, that will narrow the search-space for lead types and may narrow the orientation/location of the lead with respect to the target volume TV.

FIGS. 22a, 22b and 22c show a possible workflow for the method for planning and/or providing a therapy for neural applications, especially a neurostimulation and/or neurorecording applications in the field of Deep Brain Stimulation may be conducted, comprising at least the shown three steps:

In a first step as shown in FIG. 22a a medical image 500 is provided and visualized by the visualization means 430. Within this medical image 500 a relevant brain region 510 is marked in a first manner and/or colour (e.g. in red). This can be done by means of the input means (not shown) of the system 10.

In a second step as shown in FIG. 22b a physician specifies the intended therapy coverage area 520 in a second manner and/or colour (e.g. in yellow).

Then, in a third step the system 10 as shown in FIG. 22c suggests the therapy delivery means 300 with the required therapy parameter settings (lower panel), the implantation location of this therapy delivery means 300 (upper panel, dot—here grey dot) and the resulting volume of tissue where therapy will be delivered.

Especially, in connection with the fourth alternative system for planning and/or providing a therapy for neural applications the following aspects are explicitly disclosed:

1. A system (10) for planning and/or providing a therapy for neural applications, especially for neurostimulation and/or neurorecording applications, comprising and/oder being connected and/or being connectable to at least one therapy delivery means (300) being capable to influence a volume of tissue of a patient (1), further comprising a steering and/or field shaping means (400) which is configured such that at least the shape of the volume of tissue (TV) that shall be influenced by the at least one therapy delivery means (300) may be modelled and the necessary settings and/or implantation conditions of therapy delivery means (300) may be set accordingly.

2. The system (10) according to aspect 1 of the fourth alternative system, wherein the system (10) comprises at least one processing means (410) being capable to combine specific anatomical data and/or functional data and information about the volume of tissue (TV) of a patient (1) that can be influenced by the at least one therapy delivery means (300), wherein the at least one steering and/or field shaping means (400) is configured such that the therapy delivered by the therapy delivery means (300) may be steered depending on at least one output of the processing means (410).

3. The system (10) according to aspect 1 or 2 of the fourth alternative system, wherein the therapy delivery means (300) is or comprises a drug delivery system and/or a system for delivery of ultrasound energy like an array of transducers for delivery of ultrasound energy and/or a light-emitting system like an array of light-conductors, in particular e.g. waveguides.

4. The system (10) according to one of the preceding aspects of the fourth alternative system, in particular according to aspect 1 or 2 of the fourth alternative system, wherein the therapy delivery means (300) is or comprises a lead (300) for neural applications, especially for neurostimulation and/or neurorecording applications.

5. The system (10) according to aspect 4 of the fourth alternative system, wherein the lead (300) comprises a plurality of electrodes (132), wherein the lead (300) is capable to provide and/or generate at least one stimulation field (F), wherein especially the plurality of electrodes (132) forms a complex geometrical array and/or that the plurality of electrodes (132) is arranged circumferentially around at least one section of the lead (300), especially around a section next to the distal tip end of the lead (300).

6. The system (10) according to one of the preceding aspects of the fourth alternative system, wherein the system (10) comprises a visualization means (430), wherein the visualization means (430) is capable to visualize volume of tissue (TV) of a patient (1) to be addressed by the therapy delivery means (300), especially in the context of the pre-operative and/or peri-operative images of the patient (1).

7. The system (10) according to aspect 6 of the fourth alternative system, wherein the visualization means (430) comprises input means and output means and is configured such that patient images may be loaded and/or displayed by means of the output means and that by means of the input means a target volume of tissue (TV) of a patient (1) may be indicated, especially via voxel painting and/or by free-form drawing of 3D volumes on the patient images.

8. The system (10) according to aspect 7 of the fourth alternative system, wherein the system comprises an identifying means which is configured such that from the indicated target volume of tissue (TV) of a patient (1) the most optimal settings and/or implantation conditions of therapy delivery means (300) may be identified and especially set accordingly by the steering means (400).

9. The system (10) according to one of aspects 6 to 8 of the fourth alternative system, wherein the visualization means (430) is configured such that at least one or more effective shape of the volume of tissue (TV) may be displayed and that the system (10) comprises a simulation means (440) which is capable to provide a feed-forward simulation of the shape of the volume of tissue (TV) that shall be provided by the at least one therapy delivery means (300) and that visualization means (430) is configured such that patient images may be combined with a feed-forward simulation of the shape of the volume of tissue (TV) that shall be provided by the at least one therapy delivery means (300).

10. The system (10) according to aspect 9 of the fourth alternative system, wherein the simulation means (440) is configured such that information about tissue anisotropy and/or tissue inhomogenity is used for the simulation when providing a feed-forward simulation of the shape of the volume of tissue (TV) that shall be provided by the at least one therapy delivery means (300).

11. The system (10) according to one of aspects 6 to 10 of the fourth alternative system, wherein the visualization means (430) is configured such that the user may identify a target area and may outline a desired shape of the volume of tissue (TV) that shall be influenced by the at least one therapy delivery means (300), wherein especially the desired shape of the volume of tissue (TV) that shall be influenced by the at least one therapy delivery means (300) is a desired electrical field coverage volume.

12. The system (10) according to one of the preceding aspects of the fourth alternative system, wherein the steering and/or field shaping means (400) is configured such that at least one boundary-condition may be input, wherein especially the boundary-condition may be input via the input means.

13. The system (10) according to aspect 12 of the fourth alternative system, wherein the boundary condition is a certain range of lead-implantation angles and/or a lead position relative to the target volume (TV) (e.g. lateral to the TV) and/or a certain area to remain unaffected by stimulation.

14. The system (10) according to one of the preceding aspects of the fourth alternative system, wherein the steering and/or field shaping means (400) is configured such that at least the shape of the volume of tissue (TV) that shall be influenced by the at least one therapy delivery means (300) may be modelled and the necessary settings and/or implantation conditions of therapy delivery means (300) may be set accordingly semi-automatically and/or automatically.

15. A system for neural applications (100), especially a system for neurostimulation and/or neurorecording applications (100), for instance a deep brain stimulation system (100), the system for neural applications (100) comprising at least one system (10) for planning and/or providing a therapy for neural applications according to one of the preceding aspects of the fourth alternative system.

The invention claimed is:

1. A system for neural applications, the system comprising:
one or more processors configured to:
receive, via at least one input point of a plurality of input points arranged at respective radial positions on a single plane around an axial view of a lead visualized on a display, an indication of a user input defining a stimulation field characteristic at a user defined radial distance away from the lead, the lead comprising a plurality of electrodes configured to deliver stimulation to a patient, wherein each input point is configured to be switched by the user between two or more states of the stimulation field characteristic, and wherein the stimulation field characteristic comprises at least one of a stimulation amplitude, a stimulation energy, or a pulse-width; and
adjust at least one characteristic parameter of stimulation deliverable by at least some electrodes of the plurality of electrodes to establish at least one stimulation field defined by the stimulation field characteristic at the user defined radial distance away from the lead.

2. The system of claim 1, wherein the one or more processors are configured to automatically adjust the stimulation field according to the stimulation field characteristic at the user defined radial distance away from the lead.

3. The system of claim 1, wherein the stimulation field characteristic comprises at least one of an activation of neurons caused by the at least one stimulation field or a field strength of the at least one stimulation field.

4. The system of claim 1, wherein the plurality of electrodes at least one of forms a complex geometrical array or is arranged circumferentially around at least one section of the lead.

5. The system of claim 1, further comprising a user interface configured to:
display the plurality of input points radially arranged on a single plane around the visualization of the lead;
receive the user input inputting the at least one characteristic parameter of the stimulation field; and
display the visualization of the lead and the at least one stimulation field, wherein the user interface is configured to provide a geometrical interrelation of the user input and visualization of the lead and the at least one stimulation field.

6. The system of claim 5, wherein the user interface is configured to display the at least one stimulation field around an axial top view of the lead.

7. The system of claim 5, wherein the user interface comprises the one or more input points radially arranged on a single plane around the visualization of the lead, and wherein the one or more input points are individually selectable to adjust a respective radial direction of the at least one stimulation field.

8. The system of claim 5, wherein the user interface provides the geometrical interrelation of the user input and the visualization such that the visualization of the lead and the visualization of the at least one stimulation field is arranged in a center of a display of the user interface and in a center of a circle defined by the plurality of input points on the single plane, and wherein the user interface is configured to display a longitudinal axis of the lead in an axial top view in the center of the circle defined by the plurality of input points and display the at least one stimulation field on an isosurface level identical to a level defined by the plurality of input points.

9. The system of claim 5, wherein the user interface comprises at least one touch screen, and wherein the touch screen is configured to receive the user input and display the lead and the at least one stimulation field.

10. The system of claim 1, wherein the one or more processors are configured to calculate a stimulation field for a unit amplitude applied to a specific set of user defined active electrode contacts.

11. The system of claim 1, wherein a maximum electric field strength that should be distributed at a radial distance from the lead is user defined.

12. The system of claim 1, wherein the one or more processors are configured to measure a maximum electric field strength at a radial distance from the lead in a finite element simulation.

13. The system of claim 12, wherein the one or more processors are configured to calculate a ratio between the measured maximum electric field strength and a desired field strength at the radial distance from the lead.

14. The system of claim 13, wherein the one or more processors are configured to multiply a unit amplitude used during a simulation of the at least one stimulation field with the ratio between the measured maximum electric field strength and the desired field strength at the radial distance from the lead to calculate an amplitude required to produce the desired field strength of a desired stimulation field.

15. The system of claim 1, further comprising an implantable pulse generator and the lead, wherein the implantable pulse generator is configured to generate and deliver the stimulation field via the lead.

16. The system of claim 1, wherein the two or more states of the stimulation field characteristic comprise at least two of an on state, an off state, a half state, or a quarter state.

17. A system comprising:
one or more processors configured to:
receive, via at least one input point of a plurality of input points arranged at respective radial positions on a single plane around an axial view of a lead visualized on a display, an indication of a user input defining a stimulation field characteristic at a user defined radial distance away from the lead, the lead comprising a plurality of electrodes configured to deliver stimulation to a patient, wherein each input point is configured to be switched by the user between two or more states of the stimulation field characteristic, and wherein the stimulation field characteristic comprises at least one of a stimulation amplitude, a stimulation energy, or a pulse-width; and
adjust at least one characteristic parameter of stimulation deliverable by at least some electrodes of the plurality of electrodes to establish at least one stimulation field defined by the stimulation field characteristic at the user defined radial distance away from the lead; and
an implantable neurostimulation device configured to couple to the lead and deliver stimulation via the at least some electrodes of the plurality of electrodes according to the at least one characteristic parameter.

18. The system of claim 17, wherein the implantable neurostimulation device comprises a pulse generator configured to generate and deliver, via the at least some electrodes of the plurality of electrodes, stimulation therapy comprising the at least one stimulation field.

19. A method comprising:
receiving, by one or more processors and via at least one input point of a plurality of input points arranged at respective radial positions on a single plane around an axial view of the lead visualized on a display, an indication of a user input defining a stimulation field characteristic at a user defined radial distance away from the lead, the lead comprising a plurality of electrodes configured to deliver stimulation to a patient, wherein each input point is configured to be switched by the user between two or more states of the stimulation field characteristic, and wherein the stimulation field characteristic comprises at least one of a stimulation amplitude, a stimulation energy, or a pulse-width; and
adjusting, by the one or more processors, at least one characteristic parameter of stimulation deliverable by at least some electrodes of the plurality of electrodes to establish at least one stimulation field defined by the stimulation field characteristic at the user defined radial distance away from the lead.

20. The method of claim 19, further comprising:
displaying, via a user interface, the visualization of the lead;
displaying, via the user interface, the plurality of input points radially arranged on a single plane around the visualization of the lead;
receiving, via the user interface, the user input inputting the at least one characteristic parameter of the stimulation field; and
displaying, via the user interface, the at least one stimulation field in conjunction with the visualization of the lead and the plurality of input points such that a geometrical interrelation of the user input, visualization of the lead, and the at least one stimulation field is displayed.

21. The method of claim 19, further comprising generating and delivering, via an implantable pulse generator and the lead, stimulation therapy comprising the at least one stimulation field.

* * * * *